United States Patent
Thielen et al.

(10) Patent No.: US 8,444,673 B2
(45) Date of Patent: May 21, 2013

(54) AUTOMATIC VASCULAR CLOSURE DEPLOYMENT DEVICES AND METHODS

(75) Inventors: Joseph M. Thielen, Buffalo, MN (US); Jason P. Hill, Brooklyn Park, MN (US); Mark L. Jenson, Greenfield, MN (US); Michael J. Pikus, Golden Valley, MN (US); Leonard B. Richardson, Brooklyn Park, MN (US); Joel Groff, Montrose, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 184 days.

(21) Appl. No.: 13/025,356

(22) Filed: Feb. 11, 2011

(65) Prior Publication Data

US 2011/0196388 A1    Aug. 11, 2011

Related U.S. Application Data

(60) Provisional application No. 61/337,748, filed on Feb. 11, 2010.

(51) Int. Cl.
*A61B 17/04* (2006.01)
*A61B 17/08* (2006.01)

(52) U.S. Cl.
USPC .................................. 606/232; 606/213

(58) Field of Classification Search
USPC ................... 606/213, 214, 232; 424/422–424
See application file for complete search history.

(56) References Cited

U.S. PATENT DOCUMENTS

| | | | |
|---|---|---|---|
| 4,890,612 A * | 1/1990 | Kensey | .................. 606/213 |
| 5,021,059 A | 6/1991 | Kensey et al. | |
| 5,108,421 A | 4/1992 | Fowler | |
| 5,129,882 A | 7/1992 | Weldon et al. | |
| 5,192,300 A | 3/1993 | Fowler | |
| 5,192,302 A | 3/1993 | Kensey et al. | |
| 5,221,259 A | 6/1993 | Weldon et al. | |
| 5,222,974 A | 6/1993 | Kensey et al. | |

(Continued)

FOREIGN PATENT DOCUMENTS

| | | |
|---|---|---|
| EP | 1568326 A1 | 8/2005 |
| EP | 1671591 A1 | 6/2006 |

(Continued)

OTHER PUBLICATIONS

Loffler, Jorg F., et al., "MgZnCa Glasses without Clinically Observable Hydrogen Evolution for Biodegradable Inputs," Nature Materials, 3:887-891 (Nov. 2009). On-line at www.nature.com/naturematerials.

*Primary Examiner* — Julian Woo

(74) *Attorney, Agent, or Firm* — Seager, Tufte & Wickhem LLC

(57) ABSTRACT

Methods of installing a vascular closure device, the vascular closure device adapted for sealing an opening in biological tissue and comprising an anchor, a compressible plug, a cinch and a suture, the method comprising the steps of providing an insertion sheath, inserting the insertion sheath into the opening in the biological tissue, providing a device sheath having the vascular closure device preloaded therein with a proximal portion of the suture attached to the device sheath, subsequent to the step of inserting the insertion sheath, inserting the device sheath into the insertion sheath, and retracting the insertion sheath and device sheath simultaneously, wherein during the retraction, the insertion sheath and the device sheath are fixed to one another and devices adapted to the methods.

15 Claims, 19 Drawing Sheets

U.S. PATENT DOCUMENTS

| | | | |
|---|---|---|---|
| 5,254,105 A | 10/1993 | Haaga | |
| 5,275,616 A | 1/1994 | Fowler | |
| 5,282,827 A | 2/1994 | Kensey et al. | |
| 5,290,310 A | 3/1994 | Makower et al. | |
| 5,292,332 A | 3/1994 | Lee | |
| 5,310,407 A | 5/1994 | Casale | |
| 5,312,435 A | 5/1994 | Nash et al. | |
| 5,320,639 A | 6/1994 | Rudnick | |
| 5,342,393 A | 8/1994 | Stack | |
| 5,350,399 A | 9/1994 | Erlebacher et al. | |
| 5,360,440 A | 11/1994 | Andersen | |
| 5,370,660 A | 12/1994 | Weinstein et al. | |
| 5,383,896 A | 1/1995 | Gershony et al. | |
| 5,383,899 A | 1/1995 | Hammerslag | |
| 5,391,183 A | 2/1995 | Janzen et al. | |
| 5,411,520 A | 5/1995 | Nash et al. | |
| 5,413,571 A | 5/1995 | Katsaros et al. | |
| 5,415,657 A | 5/1995 | Taymor-Luria | |
| 5,419,765 A | 5/1995 | Weldon et al. | |
| 5,437,631 A | 8/1995 | Janzen | |
| 5,441,517 A | 8/1995 | Kensey et al. | |
| 5,443,481 A | 8/1995 | Lee | |
| 5,447,502 A | 9/1995 | Haaga | |
| 5,454,833 A | 10/1995 | Boussignac et al. | |
| 5,478,326 A | 12/1995 | Shiu | |
| 5,478,352 A | 12/1995 | Fowler | |
| 5,486,195 A | 1/1996 | Myers et al. | |
| 5,490,859 A | 2/1996 | Mische et al. | |
| 5,501,694 A | 3/1996 | Ressemann et al. | |
| 5,529,577 A | 6/1996 | Hammerslag | |
| 5,531,759 A | 7/1996 | Kensey et al. | |
| 5,540,707 A | 7/1996 | Ressemann et al. | |
| 5,540,715 A | 7/1996 | Katsaros et al. | |
| 5,545,178 A | 8/1996 | Kensey et al. | |
| 5,549,633 A | 8/1996 | Evans et al. | |
| 5,571,181 A | 11/1996 | Li | |
| 5,573,518 A | 11/1996 | Haaga | |
| 5,591,204 A | 1/1997 | Janzen et al. | |
| 5,593,422 A | 1/1997 | Muijs Van de Moer et al. | |
| 5,601,602 A | 2/1997 | Fowler | |
| 5,613,974 A | 3/1997 | Andreas et al. | |
| 5,620,461 A | 4/1997 | Muijs Van de Moer et al. | |
| 5,626,601 A | 5/1997 | Gershony et al. | |
| 5,630,833 A | 5/1997 | Katsaros et al. | |
| 5,649,959 A | 7/1997 | Hannam et al. | |
| 5,653,730 A | 8/1997 | Hammerslag | |
| 5,662,681 A | 9/1997 | Nash et al. | |
| 5,676,689 A | 10/1997 | Kensey et al. | |
| 5,700,277 A | 12/1997 | Nash et al. | |
| 5,707,393 A | 1/1998 | Kensey et al. | |
| 5,716,375 A | 2/1998 | Fowler | |
| 5,725,498 A | 3/1998 | Janzen et al. | |
| 5,725,551 A | 3/1998 | Myers et al. | |
| 5,728,114 A | 3/1998 | Evans et al. | |
| 5,728,122 A | 3/1998 | Leschinsky et al. | |
| 5,728,133 A | 3/1998 | Kontos | |
| 5,728,134 A | 3/1998 | Barak | |
| 5,741,223 A | 4/1998 | Janzen et al. | |
| 5,782,860 A | 7/1998 | Epstein et al. | |
| 5,810,884 A | 9/1998 | Kim | |
| 5,830,130 A | 11/1998 | Janzen et al. | |
| 5,836,868 A | 11/1998 | Ressemann et al. | |
| 5,843,124 A | 12/1998 | Hammerslag | |
| 5,853,421 A | 12/1998 | Leschinsky et al. | |
| 5,861,004 A | 1/1999 | Kensey et al. | |
| 5,871,474 A | 2/1999 | Hermann et al. | |
| 5,871,501 A | 2/1999 | Leschinsky et al. | |
| 5,897,567 A | 4/1999 | Ressemann et al. | |
| 5,906,631 A | 5/1999 | Imran | |
| 5,916,236 A | 6/1999 | Muijs Van de Moer et al. | |
| 5,922,009 A | 7/1999 | Epstein et al. | |
| 5,935,147 A | 8/1999 | Kensey et al. | |
| 5,947,997 A | 9/1999 | Pavcnik et al. | |
| 5,948,425 A | 9/1999 | Janzen et al. | |
| 5,951,583 A | 9/1999 | Jensen et al. | |
| 5,957,952 A | 9/1999 | Gershony et al. | |
| 6,007,561 A | 12/1999 | Bourque et al. | |
| 6,017,359 A | 1/2000 | Gershony et al. | |
| 6,045,569 A | 4/2000 | Kensey et al. | |
| 6,045,570 A | 4/2000 | Epstein et al. | |
| 6,048,357 A | 4/2000 | Kontos | |
| 6,048,358 A | 4/2000 | Barak | |
| 6,054,569 A | 4/2000 | Bennett et al. | |
| 6,056,768 A | 5/2000 | Cates et al. | |
| 6,056,769 A | 5/2000 | Epstein et al. | |
| 6,056,770 A | 5/2000 | Epstein et al. | |
| 6,080,183 A | 6/2000 | Tsugita et al. | |
| 6,110,184 A | 8/2000 | Weadock | |
| 6,120,524 A | 9/2000 | Taheri | |
| 6,126,675 A | 10/2000 | Shchervinsky et al. | |
| 6,162,240 A | 12/2000 | Cates et al. | |
| 6,179,863 B1 | 1/2001 | Kensey et al. | |
| 6,183,496 B1 | 2/2001 | Urbanski | |
| 6,190,400 B1 | 2/2001 | Van de Moer et al. | |
| 6,261,309 B1 | 7/2001 | Urbanski | |
| 6,287,332 B1 | 9/2001 | Bolz et al. | |
| 6,296,632 B1 | 10/2001 | Luscher et al. | |
| 6,296,657 B1 | 10/2001 | Brucker | |
| 6,296,658 B1 | 10/2001 | Gershony et al. | |
| 6,306,243 B1 | 10/2001 | Clark et al. | |
| 6,325,789 B1 | 12/2001 | Janzen et al. | |
| 6,350,274 B1 | 2/2002 | Li | |
| 6,368,300 B1 | 4/2002 | Fallon et al. | |
| 6,368,341 B1 | 4/2002 | Abrahamson | |
| 6,425,911 B1 | 7/2002 | Akerfeldt et al. | |
| 6,461,346 B1 | 10/2002 | Buelna | |
| 6,464,712 B1 | 10/2002 | Epstein et al. | |
| 6,468,293 B2 | 10/2002 | Bonutti et al. | |
| 6,475,177 B1 | 11/2002 | Suzuki | |
| 6,475,230 B1 | 11/2002 | Bonutti et al. | |
| 6,500,152 B1 | 12/2002 | Illi | |
| 6,508,828 B1 | 1/2003 | Akerfeldt et al. | |
| 6,524,328 B2 | 2/2003 | Levinson | |
| 6,527,734 B2 | 3/2003 | Cragg et al. | |
| 6,537,299 B1 | 3/2003 | Hogendijk et al. | |
| 6,540,735 B1 | 4/2003 | Ashby et al. | |
| 6,569,187 B1 | 5/2003 | Bonutti et al. | |
| 6,572,635 B1 | 6/2003 | Bonutti et al. | |
| 6,592,608 B2 | 7/2003 | Fisher et al. | |
| 6,596,012 B2 | 7/2003 | Akerfeldt et al. | |
| 6,596,014 B2 | 7/2003 | Levinson et al. | |
| 6,613,070 B2 | 9/2003 | Redmond et al. | |
| 6,623,509 B2 | 9/2003 | Ginn | |
| 6,632,238 B2 | 10/2003 | Ginn et al. | |
| 6,656,207 B2 | 12/2003 | Epstein et al. | |
| 6,663,650 B2 | 12/2003 | Sepetka et al. | |
| 6,663,655 B2 | 12/2003 | Ginn et al. | |
| 6,682,489 B2 | 1/2004 | Tenerz et al. | |
| 6,685,727 B2 | 2/2004 | Fisher et al. | |
| 6,699,261 B1 | 3/2004 | Cates et al. | |
| 6,712,837 B2 | 3/2004 | Åkerfeldt et al. | |
| 6,733,515 B1 | 5/2004 | Edwards et al. | |
| 6,743,195 B2 | 6/2004 | Zucker | |
| 6,749,621 B2 | 6/2004 | Pantages et al. | |
| 6,764,500 B1 | 7/2004 | Muijs Van de Moer et al. | |
| 6,780,197 B2 | 8/2004 | Roe et al. | |
| 6,790,220 B2 | 9/2004 | Morris et al. | |
| 6,818,008 B1 | 11/2004 | Cates et al. | |
| 6,824,545 B2 | 11/2004 | Sepetka et al. | |
| 6,860,895 B1 | 3/2005 | Akerfeldt et al. | |
| 6,863,680 B2 | 3/2005 | Ashby | |
| 6,890,342 B2 | 5/2005 | Zhu et al. | |
| 6,890,343 B2 | 5/2005 | Ginn et al. | |
| 6,896,692 B2 | 5/2005 | Ginn et al. | |
| 6,929,655 B2 | 8/2005 | Egnelov et al. | |
| 6,939,363 B2 | 9/2005 | Åkerfeldt | |
| 6,942,684 B2 | 9/2005 | Bonutti | |
| 6,955,683 B2 | 10/2005 | Bonutti | |
| 6,964,658 B2 | 11/2005 | Ashby et al. | |
| 6,969,397 B2 | 11/2005 | Ginn | |
| 7,001,398 B2 | 2/2006 | Carley et al. | |
| 7,008,439 B1 | 3/2006 | Janzen et al. | |
| 7,008,440 B2 | 3/2006 | Sing et al. | |
| 7,008,441 B2 | 3/2006 | Zucker | |
| 7,008,442 B2 | 3/2006 | Brightbill | |
| 7,025,776 B1 | 4/2006 | Houser et al. | |
| 7,037,323 B2 | 5/2006 | Sing et al. | |

| | | |
|---|---|---|
| 7,044,916 B2 | 5/2006 | Tenerz et al. |
| 7,083,635 B2 | 8/2006 | Ginn |
| 7,192,436 B2 | 3/2007 | Sing et al. |
| 7,267,679 B2 | 9/2007 | McGuckin, Jr. et al. |
| 7,285,126 B2 | 10/2007 | Sepetka et al. |
| 7,316,704 B2 | 1/2008 | Bagaoisan et al. |
| 7,322,976 B2 | 1/2008 | Yassinzadeh |
| 7,331,979 B2 | 2/2008 | Khosravi et al. |
| 7,331,981 B2 | 2/2008 | Cates et al. |
| 7,335,220 B2 | 2/2008 | Khosravi et al. |
| 7,344,544 B2 | 3/2008 | Bender et al. |
| 7,527,637 B2 | 5/2009 | Sater et al. |
| 7,534,252 B2 | 5/2009 | Sepetka et al. |
| 7,686,825 B2 | 3/2010 | Hauser et al. |
| 7,691,127 B2 | 4/2010 | Yassinzadeh |
| 7,731,726 B2 | 6/2010 | Belhe et al. |
| 2002/0002889 A1 | 1/2002 | Ashby et al. |
| 2002/0016612 A1 | 2/2002 | Ashby et al. |
| 2002/0072768 A1 | 6/2002 | Ginn |
| 2002/0133123 A1 | 9/2002 | Zucker et al. |
| 2002/0198562 A1 | 12/2002 | Akerfeldt et al. |
| 2003/0023267 A1 | 1/2003 | Ginn |
| 2003/0055454 A1 | 3/2003 | Zucker et al. |
| 2003/0088271 A1 | 5/2003 | Cragg et al. |
| 2004/0073243 A1 | 4/2004 | Sepetka et al. |
| 2004/0093025 A1 | 5/2004 | Egnelov |
| 2004/0098025 A1 | 5/2004 | Sepetka et al. |
| 2004/0098044 A1 | 5/2004 | Van de Moer et al. |
| 2004/0098046 A1 | 5/2004 | Tenerz et al. |
| 2004/0172059 A1 | 9/2004 | Tenerz et al. |
| 2004/0204741 A1 | 10/2004 | Egnelov et al. |
| 2004/0215232 A1 | 10/2004 | Belhe et al. |
| 2004/0243007 A1 | 12/2004 | Tenerz et al. |
| 2005/0049619 A1 | 3/2005 | Sepetka et al. |
| 2005/0049637 A1 | 3/2005 | Morris et al. |
| 2005/0085852 A1 | 4/2005 | Ditter |
| 2005/0085855 A1 | 4/2005 | Forsberg |
| 2005/0085856 A1 | 4/2005 | Ginn |
| 2005/0096696 A1 | 5/2005 | Forsberg |
| 2005/0096697 A1 | 5/2005 | Forsberg et al. |
| 2005/0107827 A1 | 5/2005 | Paprocki |
| 2005/0121042 A1 | 6/2005 | Belhe et al. |
| 2005/0125031 A1 | 6/2005 | Pipenhagen et al. |
| 2005/0137624 A1 | 6/2005 | Fallman |
| 2005/0169974 A1 | 8/2005 | Tenerz et al. |
| 2005/0177189 A1 | 8/2005 | Ginn et al. |
| 2005/0220837 A1 | 10/2005 | Disegi et al. |
| 2005/0261760 A1 | 11/2005 | Weber |
| 2005/0267521 A1 | 12/2005 | Forsberg |
| 2005/0267528 A1 | 12/2005 | Ginn et al. |
| 2005/0267560 A1 | 12/2005 | Bates |
| 2006/0004408 A1 | 1/2006 | Morris et al. |
| 2006/0030886 A1 | 2/2006 | Clark |
| 2006/0034930 A1 | 2/2006 | Khosravi et al. |
| 2006/0047313 A1 | 3/2006 | Khanna et al. |
| 2006/0052825 A1 | 3/2006 | Ransick et al. |
| 2006/0058844 A1 | 3/2006 | White et al. |
| 2006/0064124 A1 | 3/2006 | Zhu et al. |
| 2006/0100664 A1 | 5/2006 | Pai et al. |
| 2006/0142797 A1 | 6/2006 | Egnelov |
| 2006/0173492 A1 | 8/2006 | Akerfeldt et al. |
| 2006/0178682 A1 | 8/2006 | Boehlke |
| 2006/0195137 A1 | 8/2006 | Sepetka et al. |
| 2006/0206146 A1 | 9/2006 | Tenerz |
| 2006/0217744 A1 | 9/2006 | Bender et al. |
| 2006/0229662 A1 | 10/2006 | Finkielsztein et al. |
| 2006/0229664 A1 | 10/2006 | Finkielsztein et al. |
| 2006/0229672 A1 | 10/2006 | Forsberg |
| 2006/0229673 A1 | 10/2006 | Forsberg |
| 2006/0229674 A1 | 10/2006 | Forsberg |
| 2006/0265006 A1 | 11/2006 | White et al. |
| 2006/0265007 A1 | 11/2006 | White et al. |
| 2006/0265008 A1 | 11/2006 | Maruyama et al. |
| 2007/0032823 A1 | 2/2007 | Tegg |
| 2007/0032824 A1 | 2/2007 | Terwey |
| 2007/0038244 A1 | 2/2007 | Morris et al. |
| 2007/0038245 A1 | 2/2007 | Morris et al. |
| 2007/0073345 A1 | 3/2007 | Pipenhagen et al. |
| 2007/0083231 A1 | 4/2007 | Lee |
| 2007/0083232 A1 | 4/2007 | Lee |
| 2007/0135837 A1 | 6/2007 | Yassinzadeh |
| 2007/0135842 A1 | 6/2007 | Van de Moer et al. |
| 2007/0208371 A1 | 9/2007 | French et al. |
| 2007/0219576 A1 | 9/2007 | Cangialosi |
| 2007/0219623 A1 | 9/2007 | Palmaz |
| 2007/0270942 A1 | 11/2007 | Thomas |
| 2007/0276433 A1 | 11/2007 | Huss |
| 2008/0065121 A1 | 3/2008 | Kawaura et al. |
| 2008/0071311 A1 | 3/2008 | White et al. |
| 2008/0071350 A1 | 3/2008 | Stinson |
| 2008/0097521 A1 | 4/2008 | Khosravi et al. |
| 2008/0109030 A1 | 5/2008 | Houser et al. |
| 2008/0109031 A1 | 5/2008 | Sepetka et al. |
| 2008/0114394 A1 | 5/2008 | Houser et al. |
| 2008/0188876 A1 | 8/2008 | Sepetka et al. |
| 2008/0200600 A1 | 8/2008 | Schomaker et al. |
| 2008/0215077 A1 | 9/2008 | Sepetka et al. |
| 2008/0234706 A1 | 9/2008 | Sepetka et al. |
| 2008/0262532 A1 | 10/2008 | Martin |
| 2009/0024106 A1 | 1/2009 | Morris |
| 2009/0069828 A1 | 3/2009 | Martin et al. |
| 2009/0143789 A1 | 6/2009 | Houser |
| 2009/0299393 A1 | 12/2009 | Martin et al. |
| 2010/0234883 A1 | 9/2010 | White et al. |

FOREIGN PATENT DOCUMENTS

| | | |
|---|---|---|
| WO | 8911301 A1 | 11/1989 |
| WO | 99/22646 A1 | 5/1999 |
| WO | 02053202 A1 | 7/2002 |
| WO | 2006078578 A2 | 7/2006 |
| WO | 2006124238 A2 | 11/2006 |
| WO | 2006124251 A2 | 11/2006 |
| WO | 2009/025836 A1 | 2/2009 |
| WO | 2009108750 A1 | 9/2009 |
| WO | 2010/056915 A1 | 5/2010 |

* cited by examiner

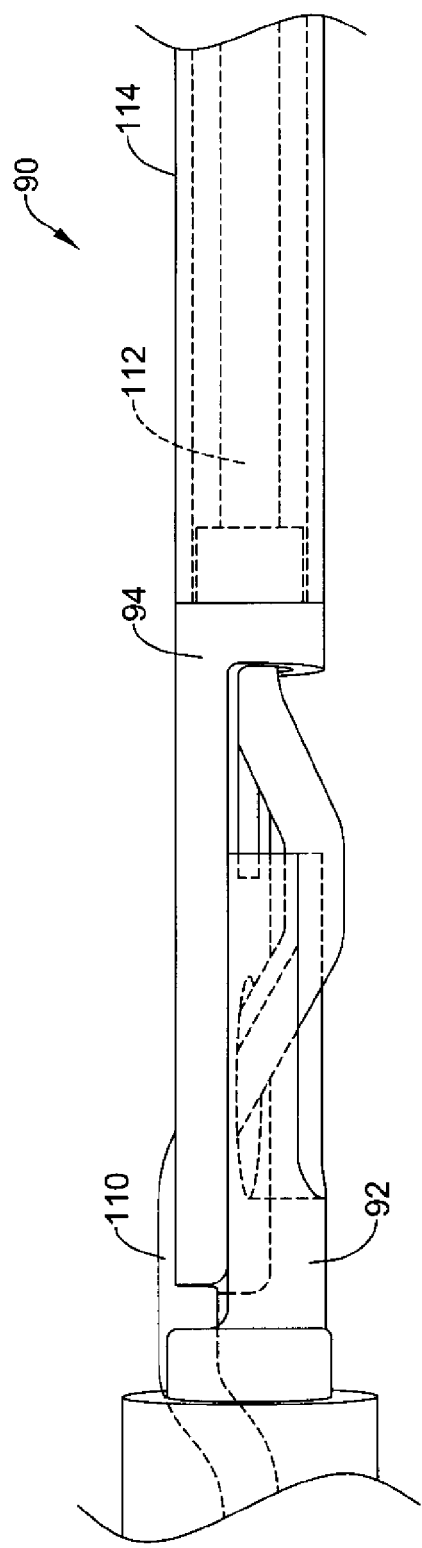
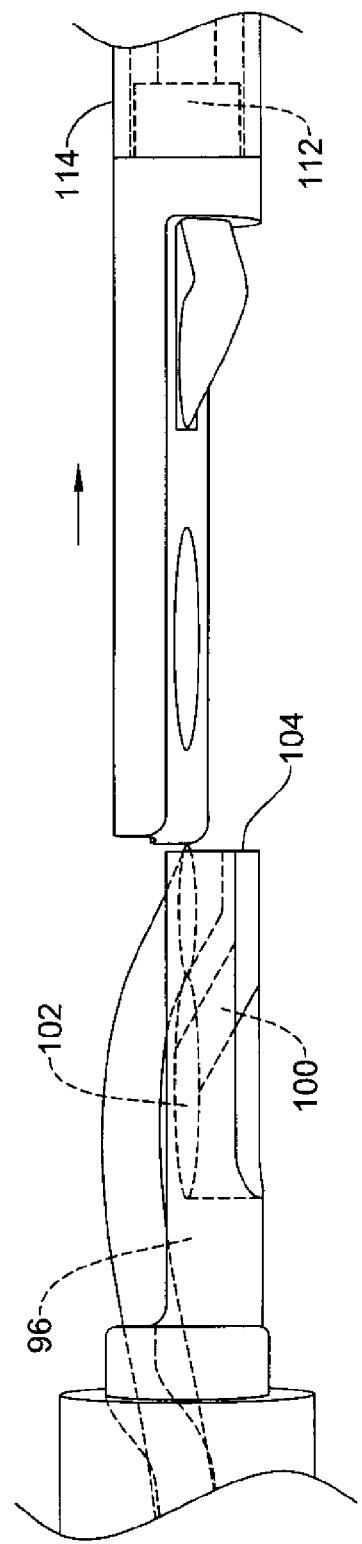
Figure 18A
Figure 18B

US 8,444,673 B2

AUTOMATIC VASCULAR CLOSURE DEPLOYMENT DEVICES AND METHODS

RELATED APPLICATIONS

This application claims priority to U.S. Provisional Application Ser. No. 61/337,748, filed Feb. 11, 2010.

FIELD OF THE INVENTION

The present invention relates generally to medical devices and methods for sealing and closing passages formed through tissue. More specifically, the present invention relates to apparatuses or devices for sealing or closing an opening formed through biological tissue to control, prevent or stop bleeding or other biological fluid or tissue.

BACKGROUND

In many medical procedures, such as, for example, balloon angioplasty and the like, an opening can be created in a blood vessel or arteriotomy to allow for the insertion of various medical devices which can be navigated through the blood vessel to the site to be treated. For example, after initial access with a hollow needle, a guidewire may first be inserted through the tissue tract created between the skin, or the epidermis, of the patient down through the subcutaneous tissue and into the opening formed in the blood vessel. The guidewire is then navigated through the blood vessel to the site of the occlusion or other treatment site. Once the guidewire is in place, an introducer sheath can be slid over the guide wire to form a wider, more easily accessible, tract between the epidermis and the opening into the blood vessel. The appropriate medical device can then be introduced over the guidewire through the introducer sheath and then up the blood vessel to the site of the occlusion or other treatment site.

Once the procedure is completed, the medical devices or other equipment introduced into the vessel can be retracted through the blood vessel, out the opening in the blood vessel wall, and out through the tissue tract to be removed from the body. The physician or other medical technician is presented with the challenge of trying to close the opening in the blood vessel and/or the tissue tract formed in the epidermis and subcutaneous tissue. A number of different device structures, assemblies, and methods are known for closing the opening in the blood vessel and/or tissue tract, each having certain advantages and disadvantages. However, there is an ongoing need to provide new and improved device structures, assemblies, and/or methods for closing and/or sealing the opening in the blood vessel and/or tissue tract.

Arteriotomy closure after diagnostic and/or interventional catheterization procedures has been addressed by a number of devices in addition to standard manual compression. One of the most successful approaches has been the use of a collagen plug placed external to the artery, held in place by a biodegradable polymer (such as PLGA) anchor inside the artery, with these two components held together by a suture which passes through the arteriotomy. The components are essentially cinched together to stabilize the components in place with arterial wall tissue pinched between the plug and anchor to maintain approximation for a period of time before sufficient clotting, tissue cohesion, and/or healing occurs to prevent significant bleeding complications. While this approach has had success, there are drawbacks with these devices. The primary problems are that bleeding complications still occur, arterial occlusion problems occur, and there are many steps required to properly implant these devices which require effort by the practitioner, training, and careful attention to various manually-performed steps to reduce the occurrence of complications. One step common to most of the prior approaches has been trimming of the cinching suture at the conclusion of the procedure. This is typically performed by pulling tension on the suture manually, depressing the skin manually, and trimming the suture manually. The suture is trimmed close to the depressed skin so that when the skin is released, the ends of the suture are underneath the surface of the skin. This is important to reduce infections which would be more likely if the suture extends to the skin because this would maintain an access path from outside the body through the normally protective skin layer to the tissues underneath. This is typically not a difficult procedure, but nevertheless represents steps which are presently performed manually, taking more time than necessary, and must be done carefully to trim the suture to the correct length. It may be desired to trim the suture a bit farther underneath the skin than is easily accomplished by this method; this may be desired to minimize infection risks, for example. The present invention overcomes these problems by providing an apparatus which automates the suture cutting, and can easily cut the suture at a location deeper under the skin if desired, providing a faster procedure and an improved safety margin for trimming location.

Prior art devices require complex techniques that require many steps to properly implant these devices. This requires training and careful attention to various manually-performed steps to reduce the occurrence of complications. The present invention overcomes these problems by providing an apparatus which automates the implantation procedure, thereby providing more reliable sealing, and reducing the complexity of using the device.

BRIEF DESCRIPTION OF THE DRAWINGS

FIG. 18A is a side view of a suture cutting mechanism with a suture therein;

FIG. 18B is a side view of a suture cutting mechanism with a cut suture therein;

DESCRIPTION

Figure 1:
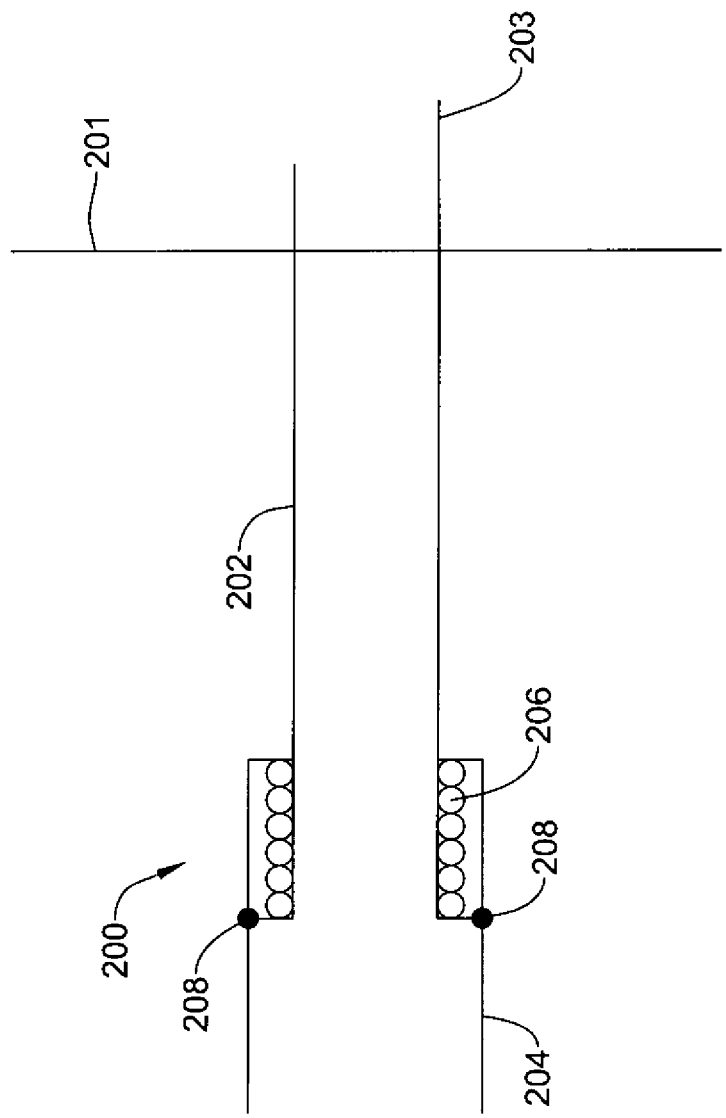
FIG. 1 is a schematic view of an introducer sheath 200 passing through a vessel wall 201.

The following summary is provided to facilitate an understanding of some of the innovative features unique to the present disclosure and is not intended to be a full description. A full appreciation of the disclosure can be gained by taking the entire specification, claims, drawings, and abstract as a whole.

The present disclosure relates generally to medical devices and more particularly to methods and devices for closing and/or sealing punctures in tissue. In one illustrative embodiment, a device is provided for delivering and deploying an anchor, plug, filament and locking mechanism adjacent to the opening in the vessel wall and/or tissue tract. In some cases, the anchor may be automatically seated against the vessel wall. In some cases, the plug is compressed and the filament is trimmed automatically. In some cases, the anchor is seated, the plug is compressed and the filament is trimmed automatically.

The invention pertains to apparatuses and methods for implantation and deployment of an anchor-plug-cinch vascular closure device. The implantation and deployment apparatus may comprise an automated plug deployment mechanism having actuation means, drive mechanism, automatic sheath retraction mechanism, automatic anchor seating mechanism, automatic cinching mechanism, optional cinching speed control means, and automated suture trimming or release. The mechanism provides automatic cinching of an extravascular plug towards an intravascular anchor with controlled plug compression. The cinching motion can be controlled to a variable rate by various means such as orifice flows or springs or electro-magnetic-mechanical speed governing to provide for reduced actuation forces to minimize damage to the plug material and the anchor. For example, a gradual acceleration or deceleration period, with different velocity or driving force than other portions of the cinching travel, can be used to avoid tearing the plug, or bending or breaking the anchor. Various steps in the deployment process are accomplished automatically in the desired sequence while minimizing required user action.

The anchor-plug-cinch vascular closure device comprises an anchor, a plug, and a cinch and is similar to those described in of application Ser. No. 12/390,241, filed Feb. 20, 2009, which is incorporated by reference in its entirety herein. The implanted components (anchor, plug, cinch) are preferably degradable so that over time they are degraded or eroded and no longer present in the body. For example, the anchor can comprise PLGA, PLLA, or PGA, but other degradable or erodable polymers can be utilized for this purpose, such as polyesters, polysaccharides polyanhidrides, polycaprolactone, and various combinations thereof, especially if a different strength—degradation time profile is desired. The cinch can comprise these materials as well; for example, a biodegradable suture can be utilized as a tension member. One or more cinching or locking elements, such as a sliding cinch disk or knot, can be utilized to secure the cinch; a bonding or latching mechanism can also be utilized to secure the cinch. The plug preferably comprises a material which swells significantly to fill space in the tissue adjacent to the artery, such as by elastic expansion, fluid absorption, chemical reaction, and so forth, so that it provides improved hemostasis. The plug can comprise the aforementioned materials as well, but collagen, gelatin, PEG, and related materials and combinations can be used also. Dense collagen material has been used for this purpose, but is relatively stiff and provides little swelling. High void-volume gelatin foam or collagen foam, PEG, and similar materials offer more compressibility for smaller-profile introduction, and/or greater swelling for improved hemostasis. Other materials can be utilized which provide for control of hydration, or thrombogenicity, to improve the function of the plug; various combinations of these can be utilized, generally degradable or erodable materials are preferred.

The implantation and deployment apparatus provides automated deployment of the anchor-plug-cinch vascular closure device. The implantation and deployment apparatus comprises elongated components for introduction of the anchor, plug, and cinch into the body, including an insertion sheath and dilator, with an orientation indicator, a hub with a hemostatic valve and an elongated thinwalled tube formed with a distal bevel to accommodate the anchor at the desired deployment angle for proper approximation to the artery. A locating mechanism is incorporated, such as a bleed path in the insertion sheath and dilator for locating the sheath at the desired location in the artery.

The implantation and deployment apparatus further comprises a device sheath which passes through the insertion sheath and is affixed to a handle. The anchor of the anchor-plug-cinch vascular closure device is disposed in or adjacent to the distal end of the device sheath for introduction into the body. The anchor is affixed to the distal end of an elongated portion of the cinch mechanism (herein referred to as the "suture"). The suture extends through the device sheath. The plug is disposed proximal to the anchor and within the device sheath and is captured or retained by the suture. A cinching or locking element (herein referred to as the "cinch disk") is disposed adjacent and proximal to the plug and within the device sheath. The implantation device also includes a push rod (typically tubular) which passes through the proximal portion of the device sheath to the plug. During the deployment procedure, the push rod, suture, plug, device sheath, and anchor pass through the insertion sheath so that the anchor just passes out the end of the insertion sheath but other components largely do not.

The handle is affixed to the device sheath and comprises a body portion, a hub connector portion, an actuation portion (optionally automatic), an automatic anchor seating mechanism, a sheath retraction mechanism (optionally automatic), an automatic cinching mechanism, and optionally comprises a suture trimming mechanism (optionally automatic); other grasping, orienting, indicating, and control elements can be incorporated.

The hub connector portion attaches to the insertion sheath hub, in a single orientation so that the relative orientation of the handle (and device sheath) and the insertion sheath (and bevel) are maintained when attached.

The actuation portion provides for arming the device and/or triggering the actions of the device. The actuation portion can include a lock or latch which is actuated by user manipulation. The actuation portion can include a latch or button which triggers the various retractions and cinching and other actions of the device in sequence. The actuation can be by application of force such as by pulling back on a portion of the delivery system after the anchor is in place in the vessel. The actions can all occur in sequence from a single trigger, or multiple triggering manipulations can be used to cause multiple sequences of device actions or single actions. Whether by manual or automatic retraction, the device is retracted until the anchor is seated snugly against the vessel wall.

The suture is attached to the automatic anchor seating mechanism. The automatic anchor seating mechanism can be activated by attachment of the hub connector portion of the handle body to the insertion sheath hub; the mechanism then retracts the suture and anchor (and may also retract other components such as the device sheath, plug, and cinch disk) relative to the introduction sheath a predetermined distance proximally to snug the anchor up against the beveled end of the insertion sheath. The automatic anchor seating mechanism can incorporate a speed limiting feature if desired to slow the movement and give the anchor sufficient time to move into alignment with the insertion sheath bevel, such as by incorporating a dashpot or other inertial or frictional mechanism; a moderate strength spring, for example, can retract the suture at an appropriate speed. The anchor seating mechanism has sufficient travel to accommodate any elongation of the suture.

The sheath retraction mechanism provides an appropriate sheath to anchor gap to allow proper deployment of the plug. Displacement can be provided to produce the desired sheath to anchor gap by paying out a predetermined length of suture, by sliding of a suture mounting element, by retraction of the device sheath hub relative to the introduction sheath hub, or by other means. Actuation of the sheath retraction mechanism can be automatically triggered, for example, by application of an appropriate retraction force by the user to pull the anchor against the vessel wall. One or more latches can be provided so that upon completion of the movement of the automatic anchor seating mechanism, automatic sheath retraction mechanism, or other mechanisms, the mechanism latches so to prevent further unwanted movement even if force is applied.

The automatic cinching mechanism advances the cinch disk, advances and axially compresses the plug (which deploys by radially expanding) and cinches the plug against the anchor. The cinching mechanism can be automatically triggered, for example, at the completion of the sheath retraction mechanism travel, or by application of an appropriate retraction force higher than the force which triggered the sheath retraction mechanism, or by manually pressing a button or releasing a latch, or by other means. The cinching mechanism also advances the cinch disk which maintains the implanted device in a cinched configuration after the procedure. When the cinching mechanism is completely actuated, the suture can be cut or otherwise released by an automatic suture cutting or release mechanism, which releases the suture from device so that the handle, device sheath, push rod, and insertion sheath can be withdrawn, leaving the anchor, plug, suture, and cinch disk in place. If an automatic suture cutting or release mechanism is not utilized, the skin is depressed an the suture trimmed to length manually so that it does not extend out past the skin.

The hub connector portion of the handle and/or the insertion sheath hub preferably have orientation features such as asymmetric shapes or pins or slots, etc., which allow the hub connector portion of the handle to mate with the insertion sheath hub in only one orientation, and which facilitate the attachment of the two pieces. Other shapes than those indicated in the drawings for the hub can be utilized, such as, for example, varying aspect ratios, angles, insertion depth, male/female, D- or squared- or rounded-components, convex/concave.

Some internal features and mechanisms which perform the described functions are not indicated in the figures to better illustrate the overall function of the invention. Such internal mechanisms can include, for example, springs, latches, levers, pulleys, strings, friction fits, dashpots, gas reservoirs.

In the embodiment described below with references to FIGS. 1-8, certain conventions are used. Figures schematically illustrate the steps. (In the figures, the bevel is not shown, and the orientation is perpendicular to the artery for simplicity of illustration. Some latches are indicated diagrammatically as dots.)

The preferred method of achieving arteriotomy closure comprises the following steps. The steps are typically, but not necessarily, performed in the order listed. Certain steps can be combined or performed separately by configuration of the internal mechanisms. Preferably, steps are performed automatically as indicated. Alternatively, certain steps could include manual actuations, although this is less advantageous.

FIG. 1 is a schematic illustration of an insertion sheath 200. The insertion sheath 200 is inserted over a guidewire after an interventional procedure (such as an angioplasty or stent deployment procedure). The insertion sheath 200 preferably includes a distal hemostatic seal (not shown) and a position indicator near the distal tip of the insertion sheath, which may provide an inlet for a bleed path which may flow through the insertion sheath to indicate the position of the insertion sheath relative to the vessel wall opening or other suitable indicator. Such features are described in the '241 application incorporated by reference above.

The insertion sheath preferably includes an insertion sheath tube 202 and an insertion sheath hub 204. In this embodiment, the insertion sheath 200 has a spring 206 or other force mechanism which can move the insertion sheath tube 202 distally relative to the insertion sheath hub 204 when the latch 208 is released in a subsequent step.

The distal end of the insertion sheath tube 202 is preferably beveled as shown at 203 and a corresponding indicator is placed on the proximal portion of the tube or on the hub so that the orientation of the bevel can be known by observation of the proximal portion of the insertion sheath. The bevel is omitted in other figures for ease of illustration.

In this step, the interventional procedure sheath is exchanged with the insertion sheath 200 and dilator over a guidewire. The insertion sheath 200 is positioned and oriented to the proper bevel angle using the orientation indicator and the distal end of the insertion sheath is positioned a predetermined distance inside the artery and past the artery wall 201 by using the bleed path or other indicator to indicate position. The insertion sheath is then held to retain proper position and the dilator and guidewire are removed.

Figure 2:
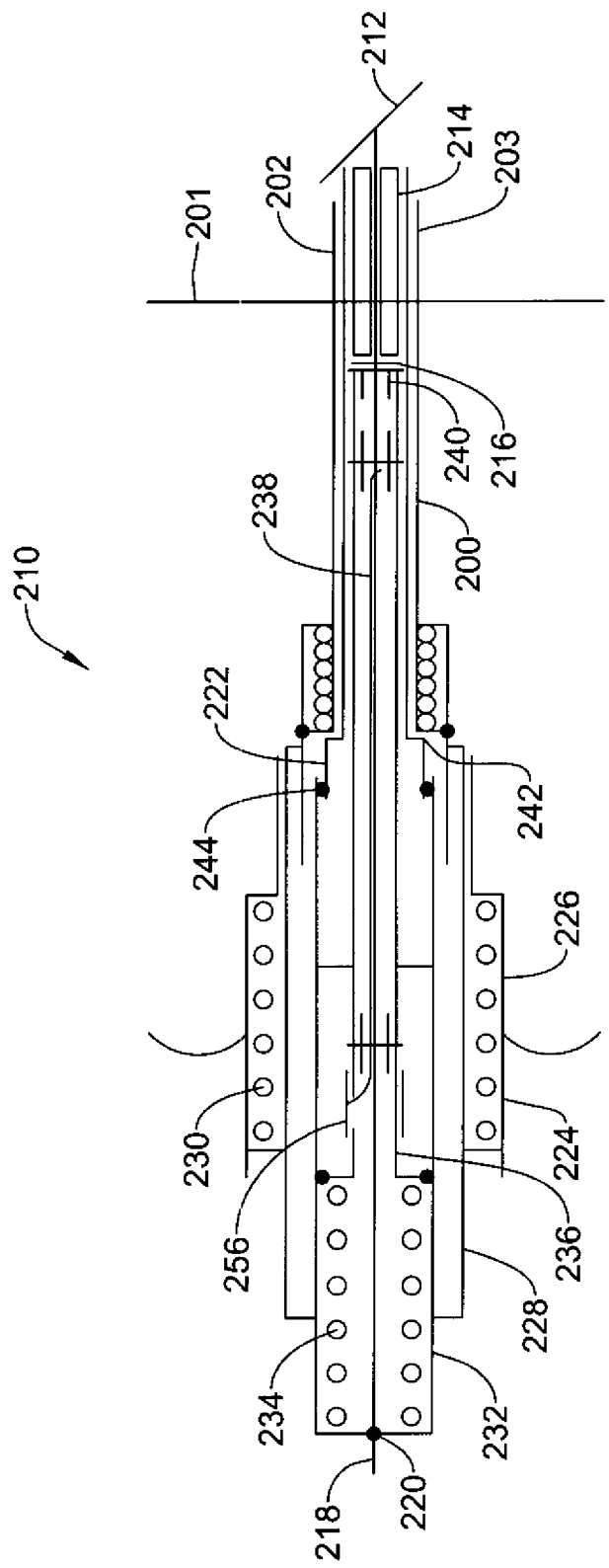
FIG. 2 is a schematic view of a device sheath 210 with a vascular closure device loaded therein inserted into the introducer sheath of FIG. 1.
Figure 3:
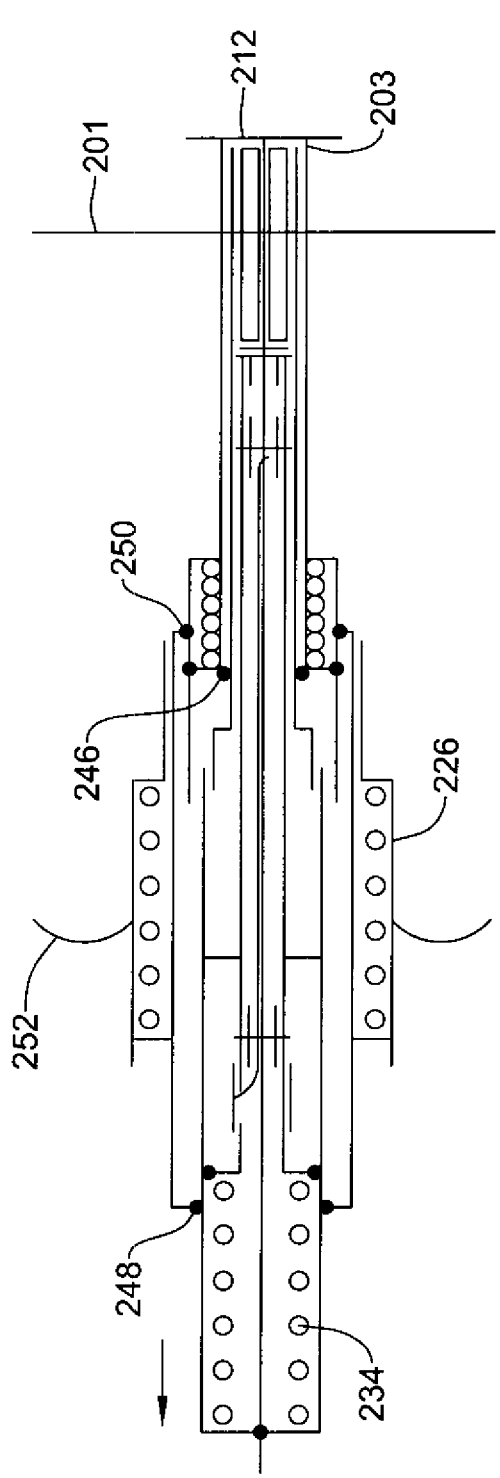
FIG. 3 is a schematic view of the introducer sheath 200 and device sheath 210 combination during a step of a process of deploying the vascular closure device.

The second step is shown schematically with reference to FIGS. 2 and 3. In this step a device sheath 210 is inserted into the insertion sheath 200 until the distal portion of the insertion sheath 200 is fed through the haemostatic valve and the device sheath 210 engages the hub 204 of the insertion sheath 200 and preferably clicks into place. The device sheath has the anchor 212, plug 214, cinch disk 216 and suture 218 preloaded. The suture is attached to the device sheath at the proximal end 220 of the device sheath.

The device sheath 210 has a device sheath tube portion 222 and a handle portion 224. The handle includes an outer portion 226 that is disposed over a first frame 228. The outer portion 226 is shown in its further distal position relative to the first frame 228 and may be slid proximally relative to the first frame 228. This proximal motion is opposed by a spring 230 disposed between the outer portion 226 and the first frame 228.

The device sheath 210 also includes a second frame 232 disposed within the first frame 228. This second frame 232 is initially fixed relative to the device sheath tube 222 and the components internal to the second frame 232 (discussed below) and may be moved relative to the first frame 228 and outer portion 226. A spring 234 is held between the proximal end of the second frame 232 and a pushing plate 236. At this point, the pushing plate 236 is still fixed to the second frame 232. The pushing plate is attached to a pushing tube 238. The pushing tube 238 has a compression plate 240 at its distalmost end, which abuts the cinch disk 216.

The anchor 212 is seated against the beveled edged 203 of the insertion sheath tube 202 by pushing the device sheath 210 against the insertion sheath 200. The device sheath tube 222 has a shoulder 242 that hits against the insertion sheath tube 202 to check the proximal movement of the device sheath tube 222. As the device sheath 210 is still being moved distally relative to the insertion sheath 200, this movement breaks a connection 244 between the device sheath tube 222 and the second frame 232. The anchor 212 is fixed to the second frame 232 by the suture 218 at the proximal end 220, and the anchor 212 therefore pushes the device sheath tube 222 proximally until the distal ends of the insertion sheath tube 202 and the device sheath tube 222 are proximate each other, as shown in FIG. 3. The components are sized such that at this point, the anchor 212 is properly seated against the beveled distal tip 203 of the insertion tube 200. When the device sheath tube 22 and the insertion sheath tube 202 are positioned so that the distal ends are proximate each other, the device sheath tube and insertion sheath tube are also fixed with respect to one another at latch 246.

The second frame 232 continues to move proximally until it latches to the first frame 228 at latch point 248, at which point the first frame and second frame are fixed relative to each other.

The device sheath 210 is move distally until the first frame 228 latches against the insertion sheath hub 204 at latch point 250, which fixes the first frame and insertion sheath hub relative to each other.

Figure 4:
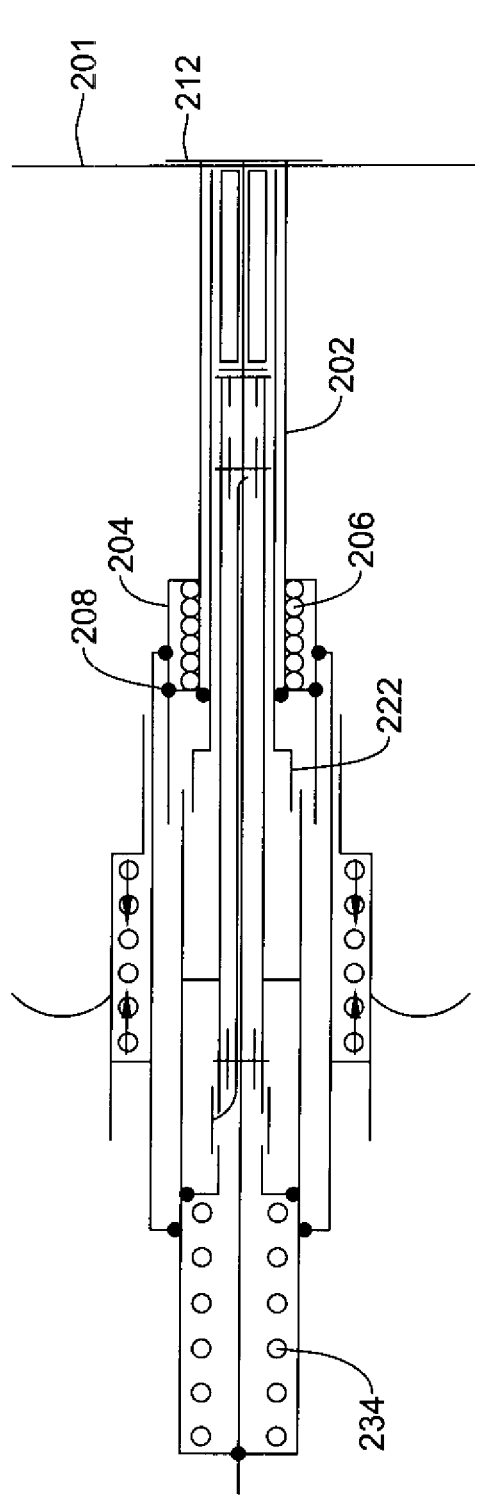
FIG. 4 is a schematic view of the introducer sheath 200 and device sheath 210 combination during a step of a process of deploying the vascular closure device.

Once the anchor 212 is seated against the distal end of the insertion sheath tube 202, the whole device (200 and 210) may be pulled proximally by pulling on the outer portion 226. This first seats the anchor plug 212 against the artery wall 201, as shown in FIG. 4. The function of the spring 230 disposed between the first frame 228 and outer portion 226 may be seen at this point. This spring 230 functions to control the amount of force transmitted from the outer portion 226 to the first frame 228.

It is helpful to recall that at this point in the process, the first frame 228 is fixedly connected to the insertion sheath hub 204 and to the second frame 232. The internal components not yet discussed are fixedly attached to the second frame 232. The insertion sheath tube 202 is fixedly attached to the device sheath tube 222. Finally, the insertion sheath tube 202 is also still attached to the insertion sheath hub 204.

Figure 5:
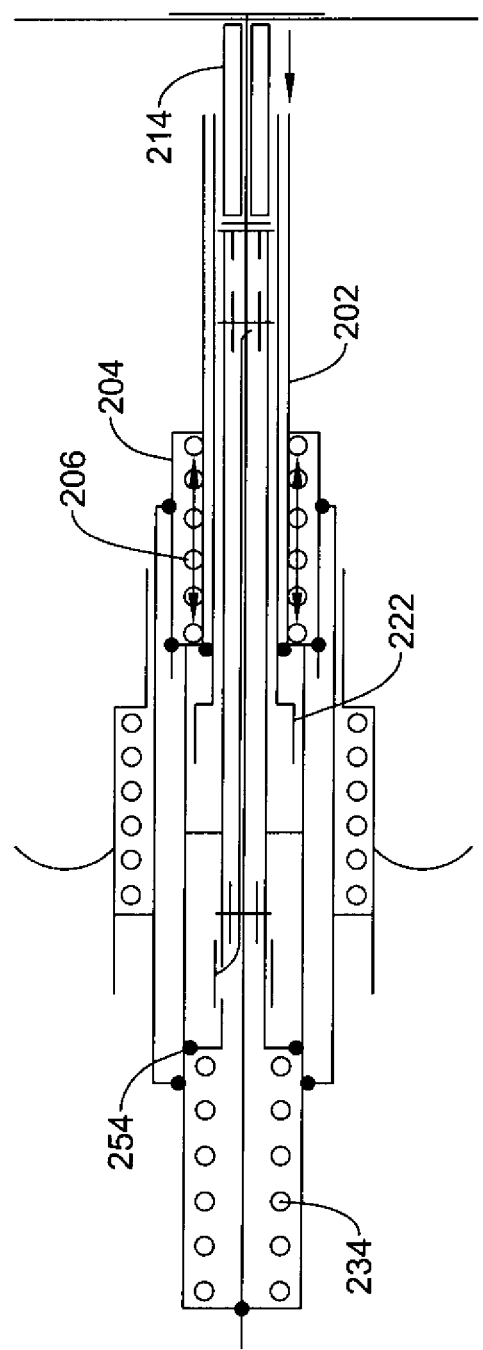
FIG. 5 is a schematic view of the introducer sheath 200 and device sheath 210 combination during a step of a process of deploying the vascular closure device.

When the device (200 and 210 together) is pulled proximally by pulling on the outer portion 226, the anchor plug 212 positioned against the artery wall 201 prevents the device from being pulled from the patient's body. A force builds up in the mechanism. When a predetermined level of force is reached, the connection 208 between the insertion sheath hub 204 and the insertion sheath tube 202 is broken. This releases the spring 206 disposed between the insertion sheath tube 202 and hub 204. This spring 206 expands to drive the insertion sheath tube 202 (and connected device sheath tube 222) proximally relative to the insertion sheath hub 204. This operates to retract the distal ends of the insertion sheath tube 202 and device sheath tube 222 from around the distal portion of the plug 214, as shown in FIG. 5.

Figure 6:
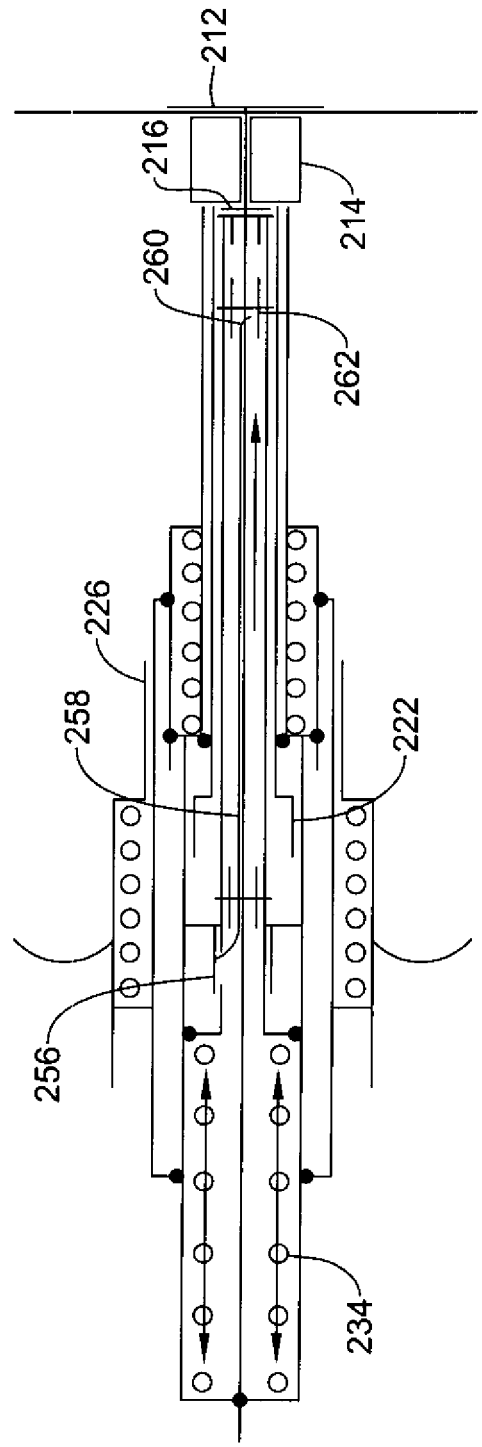
FIG. 6 is a schematic view of the introducer sheath 200 and device sheath 210 combination during a step of a process of deploying the vascular closure device.
Figure 7:
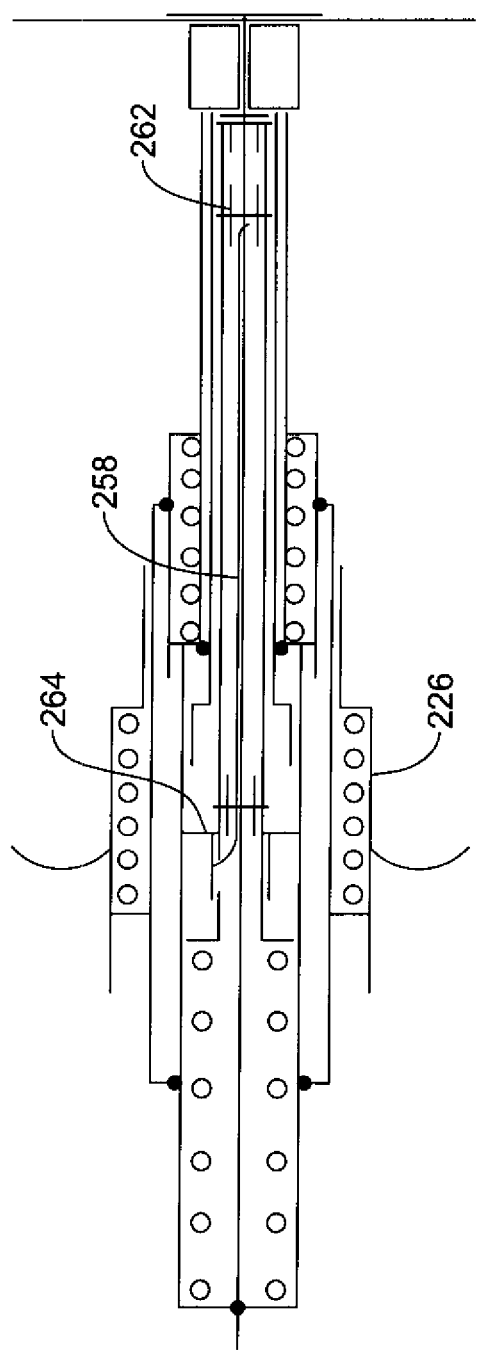
FIG. 7 is a schematic view of the introducer sheath 200 and device sheath 210 combination during a step of a process of deploying the vascular closure device.

The operator continues to pull the device (200 and 210) proximally by pulling on the outer portion 226, which further compresses the spring 230 between the outer portion 226 and the first frame 228 to provide a greater force. This causes a second connection point 254 to release, between the second frame 232 and the pushing plate 236. This allows spring 234 to expand to advance to the pushing plate 236 distally. As the pushing plate 236 is connected through the pushing tube 238 to compression plate 240 and as the suture is still connected at 220 to the second frame 232, this motion advances the cinch disk 216 to compress and deploy the plug 214. This is illustrated in FIG. 6.

There are several further components that may be attached to the pushing plate 236 and pushing tube 238. A suture cutting mechanism 256 may be friction fit to the pushing plate 236. Suture cutting mechanisms will be discussed more fully below, but for the purposes of this embodiment, it is sufficient to say that the suture cutting mechanism includes a long pull wire 258 with a blade at 260 at the distal end. The blade at the distal end is disposed in or proximate to a shearing block 262, which is fixed within the pushing tube 238. The suture or filament is threaded through the shearing block 262 and/or blade 260 such that relative movement of the shearing block 262 and blade 260 may cut the suture.

Once the connection point 254 is released, the spring 234 at the proximal end of the second frame 232 pushes the pushing plate 236 distally to advance the cinch disk 216 to compress and deploy the plug 214 as described above. This spring 234 continues to expand and forces the suture cutting mechanism 256 against a stop 264. This stop 264 is shown as part of the second frame 232. At this point, the spring 234 forces the push plate 236 proximally relative to the suture mechanism 256. Because the suture mechanism 256 is fixed to the blade 260 by the pull wire 258 and because the shearing block 262 is fixed within the push tube 238 which is still being pushed by the push plate 236, relative movement between the blade 260 and the shearing block 262 is created, which cuts the suture 218. This is illustrated schematically in FIG. 7.

Figure 8:
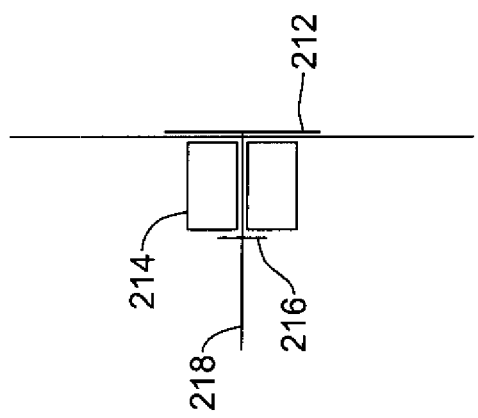
FIG. 8 is a schematic view of a deployed vascular closure device.

The device (200 and 210) is still pulled proximately by the outer portion 226. As the device is no longer attached to the anchor 212, this serves to retract the device from the body, leaving the anchor 212, plug 214, cinch disk 216 and suture 218 distal portion cinched to the artery wall to provide hemostasis, as illustrated in FIG. 8.

Since many of the actions occur automatically, the procedure is streamlined from a user perspective. The user steps condense to the following:

1. Swap the interventional sheath for the insertion sheath 200 and position the insertion sheath 200 using bleed indicator.

2. Hold the insertion sheath position, and insert the device sheath 210 until it engages the insertion sheath hub 204 (the anchor 212 automatically seats against the insertion sheath bevel 203).

3. Retract the device handle 224 to deploy the device and remove the delivery system (the sheath retraction, cinch mechanism, and suture cutting all happen automatically in sequence).

Prior art devices and procedures have more steps which must be performed by the user because certain automatic features incorporated into the present invention have previously been done manually by the user. The prior art is therefore more complicated to use. Also, the present invention accomplishes certain actions in an automatically controlled manner, making the performance of the device more reliable, less affected by the orientations, forces, and movement speeds applied by the user. For example, prior art devices typically do not have automatic seating of the anchor against the insertion sheath bevel. Also, prior art devices typically do not have automatic tension and compressive forces applied to the plug. Also, prior art devices typically do not cut the suture automatically upon proper plug deployment. These and other features streamline the use of the device and provide improved reliability over the prior art.

A second embodiment is illustrated with respect to FIGS. 9-17. One difference between this embodiment and the previous embodiment is that the step of seating the anchor plug against the distal end of the insertion sheath tube is less automatic.

Figure 9:
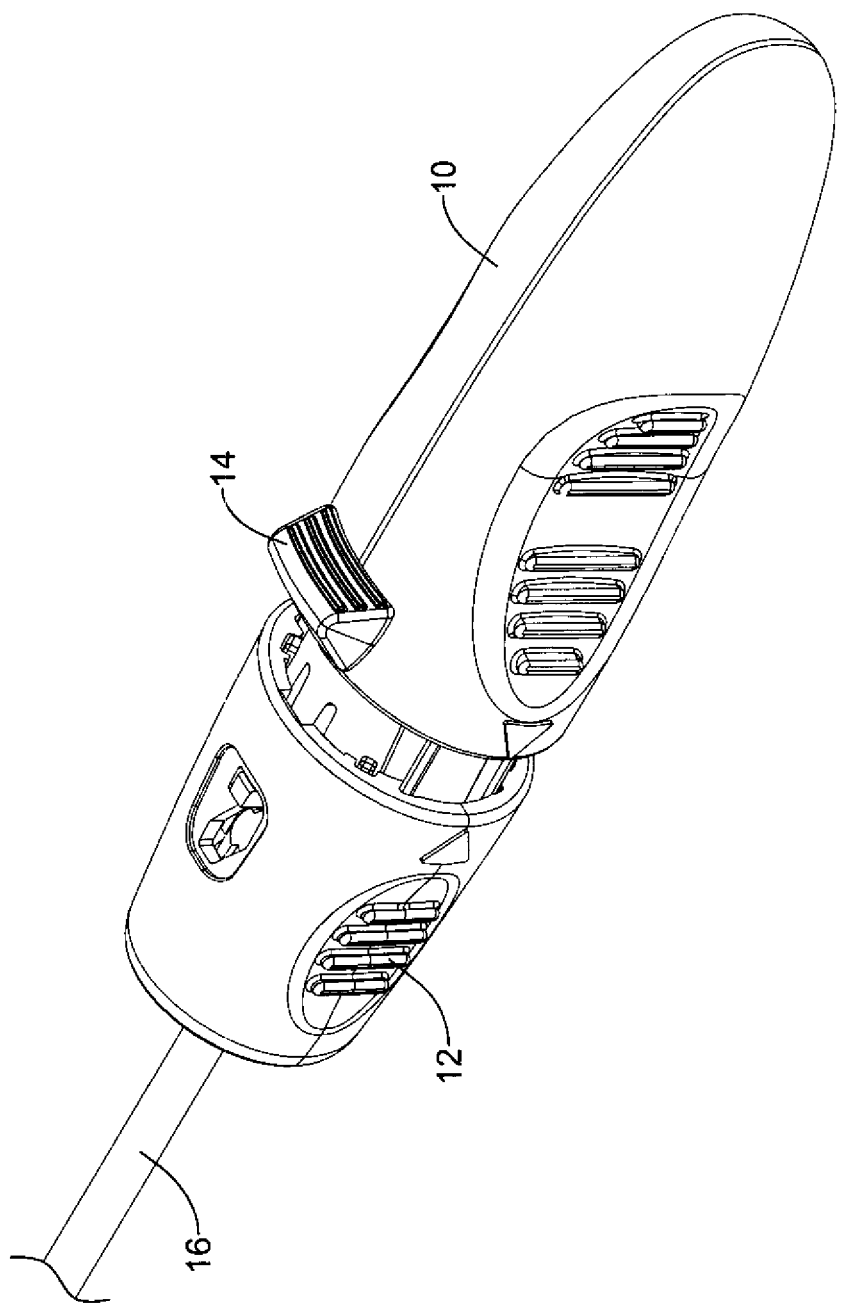
FIG. 9 is an isometric view of the proximal portion, including the handle, of a device sheath.

FIG. 9 is a view illustrating the proximal portion of a second embodiment. In FIG. 9, the proximal portion of the device sheath 10 and the proximal portion of the insertion sheath 12 are shown. The device sheath is slid into the insertion sheath tube 16 but is not yet engaged with the device sheath.

The device sheath may optionally include a button 14 or other trigger mechanism, which is pushed to allow the automated process to start. Such a button 14 may be useful to prevent premature deployment of the process.

The insertion sheath 12 preferably includes a distal hemostatic seal (not shown) and a position indication near the distal tip of the insertion sheath, which may provide an inlet for a bleed path which may flow through the insertion sheath to indicate the position of the insertion sheath relative to the vessel wall opening or other suitable indicator. Such features are described in the '241 application incorporated by reference above.

In the first step, the insertion sheath is inserted over a guidewire after an interventional procedure (such as an angioplasty or stent deployment procedure). This step is not illustrated in these figures.

Figure 10:
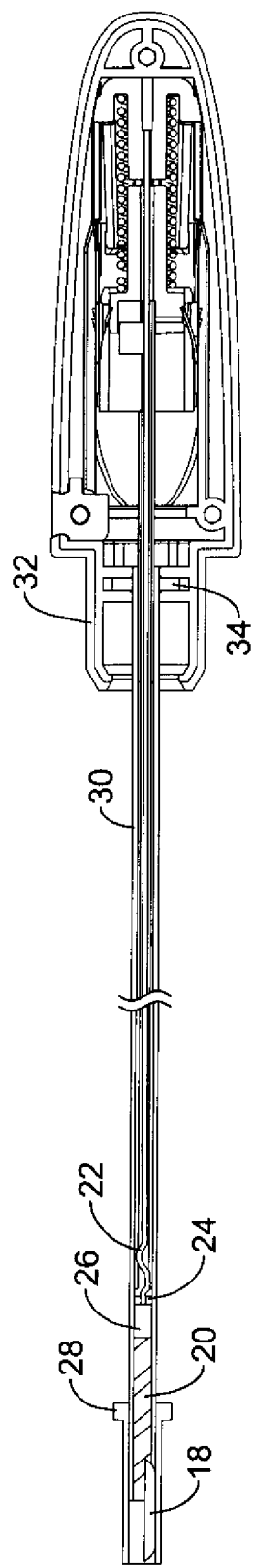
FIG. 10 is a cross-sectional view of a device sheath with a vascular closure device loaded therein.

FIG. 10 is a cross-sectional view of a device sheath similar to that of FIG. 9 prior to the insertion of the device sheath into the insertion sheath. The anchor 18, plug 20, suture 22 and cinch disk 24 are preloaded in the device sheath and the proximal end of the suture is fixed to the second frame 36. (An optional plug component 26 is shown in this figure). The anchor is kept in an insertion orientation by an orientation tube 28. The device sheath tube 30 is fixed to the outer portion 32 by a fixation disk 34 or other suitable mechanism.

Figure 11:
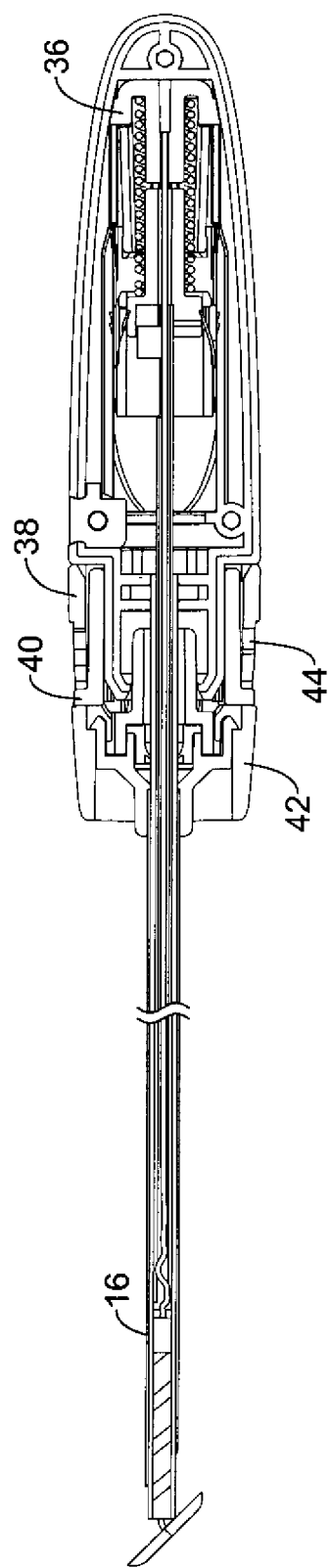
FIG. 11 is a cross-sectional view of the device sheath of FIG. 10 inserted into an introducer sheath.
Figure 12:
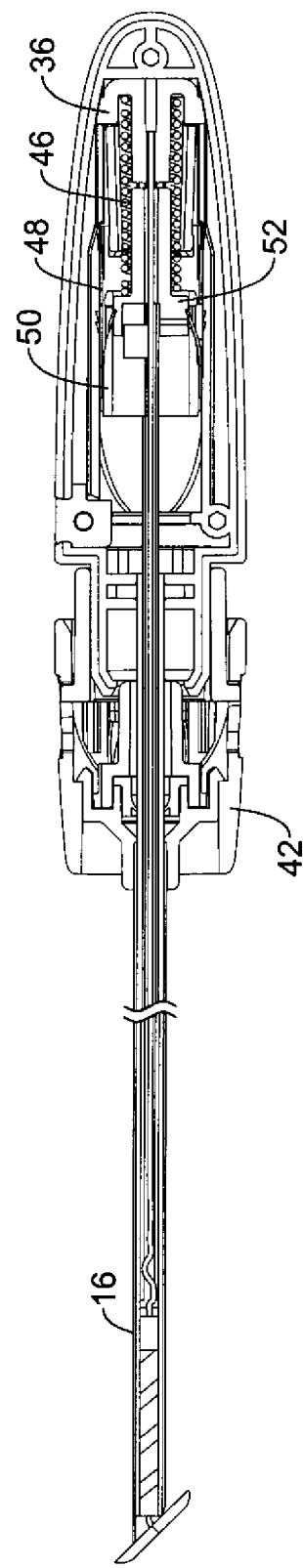
FIG. 12 is a cross-sectional view of the device sheath and introducer sheath of FIG. 11 during a step of a process of deploying the vascular closure device.
Figure 13:
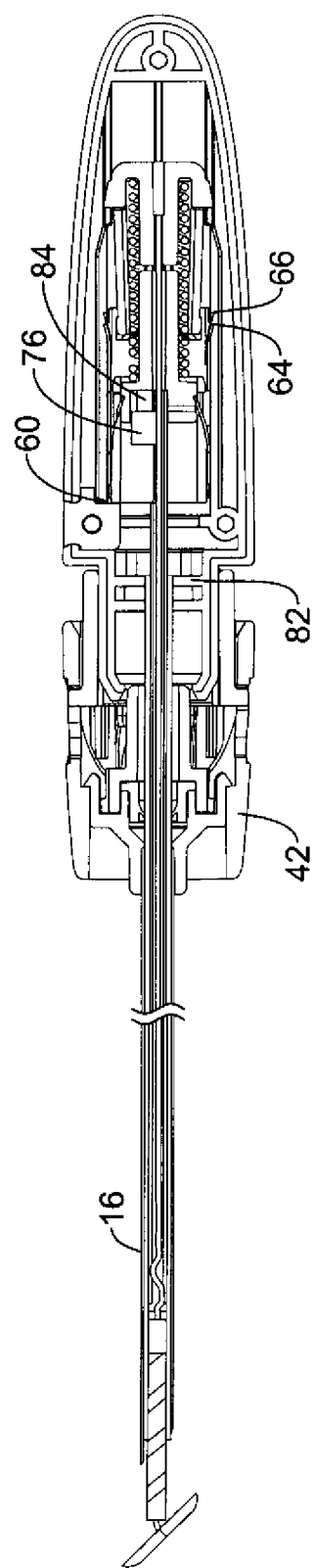
FIG. 13 is a cross-sectional view of the device sheath and introducer sheath of FIG. 11 during a step of a process of deploying the vascular closure device.

With reference to FIGS. 11 and 12, the steps of inserting the anchor through the artery wall and seating the anchor against the distal end of the insertion sheath tube are described.

While the artery wall is not illustrated in these figures, it is contemplated that prior to FIG. 11, the insertion sheath is already properly positioned through the artery wall. When the device sheath 10 is inserted into the insertion sheath 12, the insertion sheath pushes the orientation tube 28 distally. The insertion sheath tube 16 keeps the anchor 18 in an insertion orientation until it deploys through the distal tip of the insertion sheath as illustrated in FIG. 11. The orientation tube 28 is then housed within the device sheath hub 38 throughout the remainder of the procedure.

The device sheath is inserted until an insertion sheath collar 40 is locked to the device sheath by a detent (not shown) or other mechanism. This is the state in FIG. 11.

The insertion sheath is then held in place by an operator holding onto hub 42 and the device sheath 10 is retracted proximally by the operator. This moves the collar 40 relative to the hub 42 until the collar is locked in a second position by a detent 44 or other mechanism, as shown in FIG. 12. Because the insertion sheath tube 16 is fixed to the hub 42, and the anchor, plug, cinch disk, suture and device sheath tube 30 are fixed relative to the device sheath, this moves those components relative to the insertion sheath tube 16 to seat the anchor 18 against the distal end of the insertion sheath tube as shown in FIG. 12.

The operator releases the insertion sheath, and continues to withdraw the device sheath proximally. This first seats the anchor 18 against the inner wall of the artery and next starts to move the internal components of the device sheath distally relative to outer portion 32.

Figure 15:
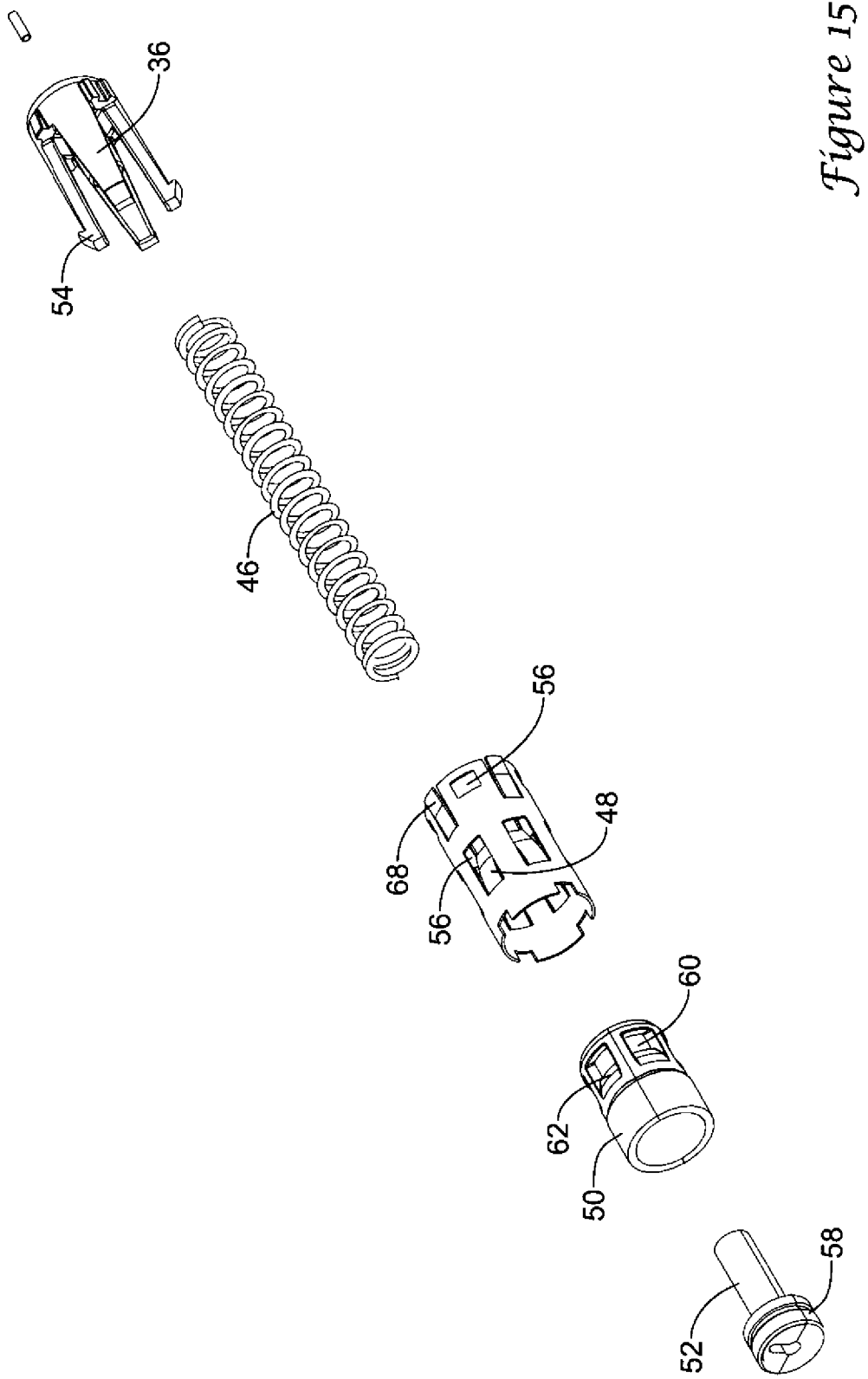
FIG. 15 is an exploded view of certain interior components of an introducer sheath.
Figure 16:
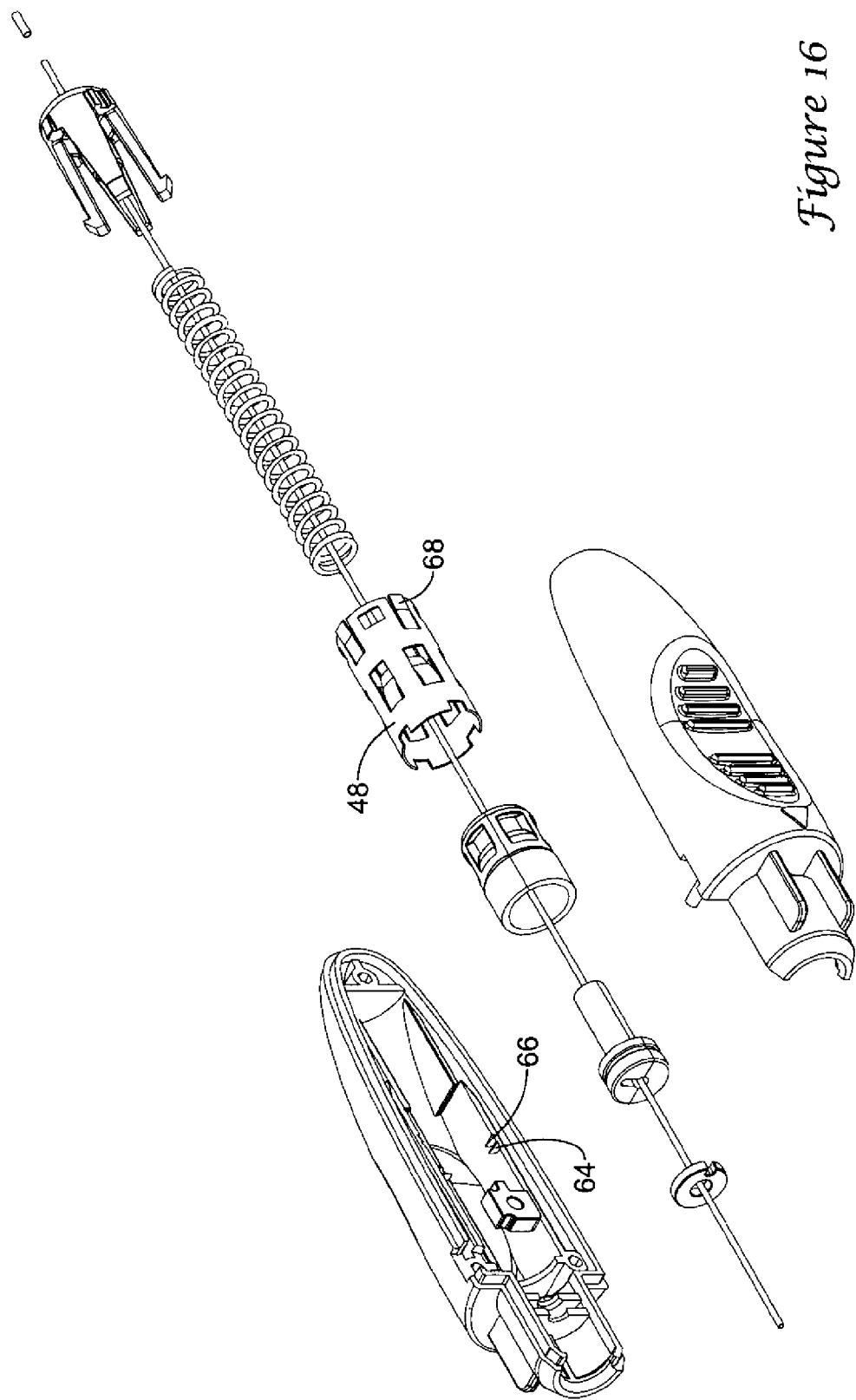
FIG. 16 is an exploded view of the proximal portion of an introducer sheath.
Figure 17:
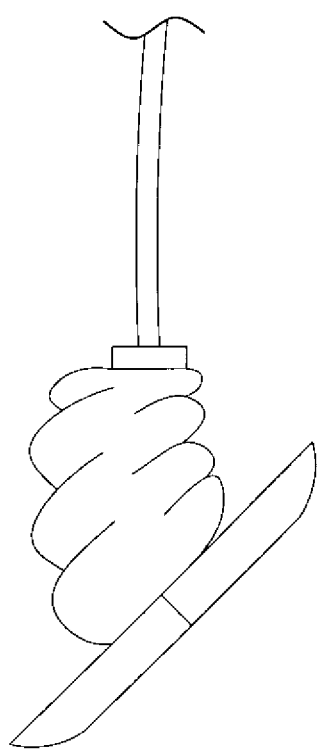
FIG. 17 is a view of a deployed vascular occluder device.

Some of those internal components can be better seen with reference to FIG. 15, which is an exploded view. Second frame 36, spring 46, first tube 48, second tube 50 and pusher plate 52 are illustrated. These components may also be seen in cross-section in FIG. 12, for example.

In the step of FIG. 12, these internal components are positioned as follows. Tabs 54 of second frame 36 are in holes 56 of first tube 48. These two components are fixed relative to each other throughout the procedure. Tabs 56 of first tube 48 are positioned through holes 60 of second tube 50 and the proximal ends of tabs 56 are disposed in slot 58 of pusher plate 52. This is a circumferential slot. The spring is captured between second frame 36 and pusher plate 52. The distal end of first tube 48 is somewhat proximal the distal end of second tube 50.

When the operator continues to withdraw the device (moving from FIG. 12 to FIG. 13), these internal components move distally relative to outer portion 32. The distal end of second tube 50 hits a stop at 60. The first tube is forced to continue moving distally by its connection to the second frame until its distal end also hits the stop at 60.

The effect of this relative movement between first and second tubes 48 and 50 is to force tabs 48 to ride up on ramps 62. This forces the proximal end of the tabs 48 radially apart, which moves them out of slot 58. This releases spring 46.

First tube 48 also includes tables 68. These tabs 68 engage detents 64 and 66 as the internal components move proximally within outer portion 32. These tabs thereby prevent the internal components from being moved distally one the detents have been reached. Detents 66 are engaged by tabs 68 when the proximal edge of the second tube 50 reaches the stop at 60. Detents 64 are engaged by tabs 68 when the proximal edge of the second tube reaches the stop at 60.

Figure 14:
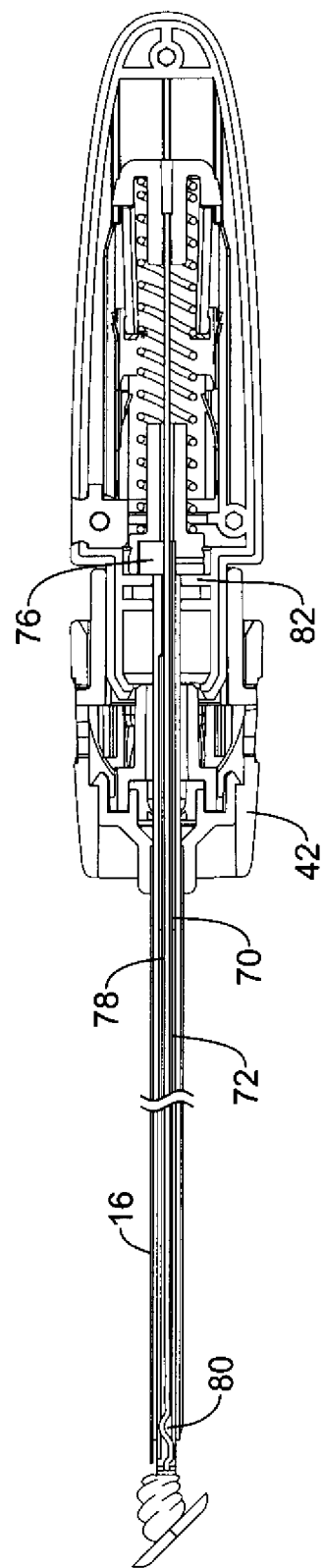
FIG. 14 is a cross-sectional view of the device sheath and introducer sheath of FIG. 11 during a step of a process of deploying the vascular closure device.

In FIG. 14, one can see the effect of releasing spring 46. Spring 46 drives pusher plate 52 distally, which pushes pusher tube 70, 72 to drive pushing end/shearing block 74 against cinch disk 24. This compresses the plug 20.

Also included in this embodiment are components related to the suture cutting mechanism. A suture cutting mechanism block 76 is connected by a tube 78 (located between the suture and the pusher tube) to a cutting block 80. The suture is threaded through the cutting block 80 and the shearing block 74. Block 76 is friction fit to pusher plate 52. When the proximal end of block 76 reaches stop 82, the block 76 is driven into a cavity 84 of the pusher plate 52. Because the pusher plate is connected by pusher tube 70, 72 to pushing end/shearing block 74, and block 76 is connected by tube 78 to cutting block 80, a relative movement is created between the shearing block 74 and the cutting block 80, which cuts the suture.

At this point the device may be withdrawn, and the anchor, suture, plug and cinch disk are installed to create hemostasis.

Another embodiment of the invention is described with reference to FIGS. 18a and 18b. These figures illustrate the distal portion of an automatic suture cutter device 90. The device 90 includes a shearing block 92 and a cutting element 94. The shearing block includes a face 96 that abuts a corresponding face 98 of the cutting element. The faces 96 and 98 may be flat or may have another complementary shape. A lumen 100 is disposed in the shearing block 92. The lumen 100 has a first opening 102 on the face 62 and a second proximal opening 104. Lumen 102 angles away from opening 102 to create a sharp edge on the proximal side of the opening 102. The cutting element 94 includes a corresponding lumen 106 with an opening 108 on face 98 and another opening (not shown) on the other side of the cutting block. Lumen 106 angles away from opening 108 to create a sharp edge on the distal side of opening 108.

The cutting element 94 and the shearing block are initially aligned such that openings 102 and 108 are aligned. A suture 110 is threaded through the openings. The cutting element may then be retracted to cut the suture. The angled edges of the openings 106 and 108 act as a scissors to shear the suture.

The cutting element may include a proximal hole 112 to receive the suture and may be attached to a tube or wire 114, which can be acted on to actuate the cutting mechanism. The shearing block 92 may include a central opening in the distal face through which the suture may be threaded. Both the shearing block and the cutting element are confined within a tube; this allows movement of the cutting element relative to the shearing block only along the direction of the arrow.

This suture cutting device may readily be incorporated into one or both of the embodiments described above. For example, shearing block 96 may correspond to shearing block 74 of the previous embodiment and cutting element 94 may correspond to cutting block 80. The suture cutting may be triggered automatically as described above.

Figure 19A:
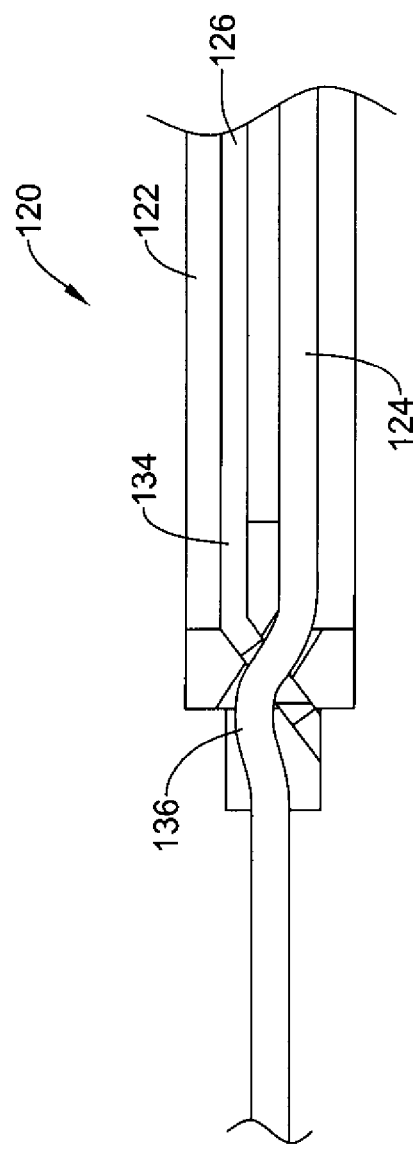
FIG. 19A is a side schematic view of a suture cutting mechanism with a suture therein.
Figure 19B:
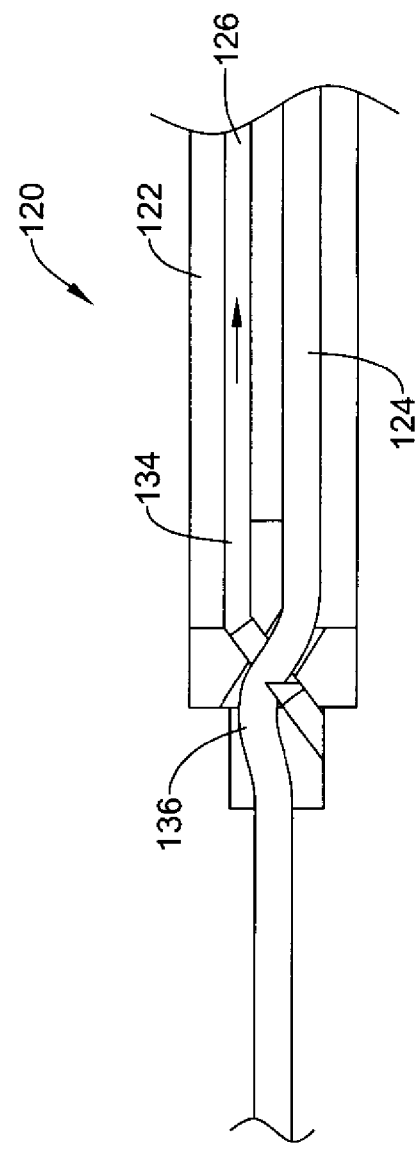
FIG. 19B is a side schematic view of a suture cutting mechanism with a partially cut suture therein.

Another embodiment 120 of an automatic cutting mechanism is shown with respect to FIGS. 19a and 19b. This embodiment includes a tube 122 that has a suture lumen 124 and a cutting wire lumen 126. A shearing block 128 is fixed to the tube and includes a first lumen 130 for the suture and a second lumen 132 for the cutting wire 134. The first and second lumens cross in the shearing block. The cutting wire 134 has a distal end disposed in the cutting block and preferably has a loop (seen in cross section) with a cutting edge 136 on the inside of the loop. The loop is sized such that in a first position (shown in FIG. 19a), the cutting wire can be positioned so that it does not impinge on lumen 130. When it is desired to cut the suture, the cutting wire 134 may be retracted proximally to sever the suture.

In this example, the shearing block has an angled hole through which the suture passes. The suture can move freely through the hole in either direction as needed by the delivery motions of the device. The cutting edge of the cutting element is initially positioned so that the suture is not contacted by the cutting edge until desired. The following figure illustrates the suture passing through the shearing block and other components. In this position, the suture is free to move relative to the cutter apparatus. The shearing block location within the device sheath, and the length of the cutting element, is chosen to cut the suture at a location long enough to minimize any risk of unintended suture release from the cinch disk, but short enough to be sufficiently far underneath the skin to minimize any risk of infection. Reduced length of suture also reduces the inflammatory response which occurs during biodegradation of a degradable suture.

The shearing block can be fixed at a particular location in the device sheath to allow enough space for the implantable portions, but little excess space. Alternatively, the shearing block can be advanced, such as together with the cinching movement, to follow the cinch disk and minimize the excess length of suture. The shearing block and cutting element can be advanced or retracted together at various stages in the deployment of the vascular closure device to provide for proper coordinated function of the deployment system. The following figure illustrates the cutter apparatus advanced along the suture; such advancement may be used during plug compression during vascular closure device deployment. The handle can have interacting features so that after the cinching movement occurs, the cutting element is automatically moved to cause the cutting of the suture. Alternatively, a manual actuator for the cutting element can be provided. The cutting movement of the cutting element can be either inward or outward, depending on the geometry of the cutting edge and shearing block. The present example shows the cutting element pulled back to cause the cutting of the suture.

After the suture is cut, the cutter mechanism is removed from the body; this motion may be combined with removal of the device sheath, handle, or other elements of the system. The removal may also be combined with retraction of the cutting element which produces the cutting, in an orderly or automatic manner. The following figure illustrates the cutting apparatus being removed after the suture has been cut. Other elements of the vascular closure device are not shown in these illustrations, but include an anchor, plug, and cinch disk, for example.

The suture cutter must be sufficiently flexible to allow for access and use; as examples, the cutter assembly extension can be made of a polymer, or slotted metal tube, which have sufficient strength but are flexible in bending.

In an automated version, the handle end of the cutting apparatus has steps, attachments, latch components, linkages or other features so that the motion of the cutter assembly extension, the cutting element, and the suture extension are actuated from the delivery system handle. The cutter can be advanced during plug compression, and the cutting element retracted to cut the suture, in a coordinated and automated manner during the device deployment sequence, using manual forces and displacements, latch release spring deployments, motor driven displacements, or other means.

The suture can be a continuous length of suture from the anchor, through the plug and cinch disk, all the way to the handle. A predetermined amount of suture extension can be accommodated, such as that obtained by a force-actuated triggering of the suture cutting. Alternatively, a shorter length of suture can be coupled to a suture extension such as a more rigid filament, wire or tube structure such as by swaging, fastening using a tubing fastener, or other bonding means. The suture extension can reduce the total displacement due to stretching of the suture during deployment of the vascular closure device, enhancing the positional control and improving the reliability of the device deployment. The shearing block can be a static structure with a hole through which the suture passes, or it can have a shape or orientation change, such as from straight to angled, to reduce friction between the suture and the shearing block during cinching, yet obtain an angled hole orientation for effective cutting. Multiple components can be used to achieve a shape change, or the shearing block can rotate to reorient the hole, or the shearing block can deform to better capture and control the suture and facilitate cutting by the cutting element. A feature incorporated with the cutting element can push or actuate an orientation change for the shearing block hole, so that the reorientation happens automatically when the cutting element is pulled back.

The cutting surface portion of the cutting element can slide with respect to the shearing block; in one relative orientation the shearing block holds the suture away from the cutting element to prevent damage to the suture. In another relative orientation the cutting element passes across the hole in the shearing block to cut the suture. For example, by pulling on the proximal end of the cutting element, which is accomplished either automatically or by actuation of the delivery device handle, the cutting element is retracted a short distance to trim the suture at the location of the shearing block. The cutting element, shearing block, and excess suture are removed with the device sheath at the conclusion of the procedure.

The shearing block can have a sharp edge rather than the cutting element, or both can have a sharp edge.

The cutting element is typically withdrawn to trim the suture to length. However, most motions of the cutting element can be reversed in orientation, so that the cutting element can be advanced a short distance to trim the suture to length. The cutting or shearing edge(s) can be oriented for close contact on advancing or on retracting of one or more elements.

The suture can take a straight path through cutter components, or the suture can be displaced to take a curved or angled path through cutter components to facilitate the cutting.

The shearing block can be advanced or withdrawn a short distance against a stationary cutting element to trim the suture to length.

A manual actuation feature such as a grasping ring can be incorporated to provide additional movement or control in case the automatic actuation fails to completely trim the suture.

The suture cutting apparatus can be modified to provide for minimally-invasive or automated cutting of sutures, even if the sutures are not associated with an anchor plug cinch type of vascular closure device.

If any mechanical advantage for compressing and deploying the plug is desired, a pulley system, or gear system, or hydraulic system, or other mechanical system can be incorporated into the handle.

Various overall configurations of the handle can be used. For example, the apparatus can be shaped like a syringe, or have an angled handle like a gun, or have concentric sliding cylinders with flanges, or have a squeeze mechanism where two portions of the handle are squeezed together to actuate the cinching mechanism, or have other configuration as is convenient for the principle actuations of components: attachment of handle to insertion sheath, and proximal movement to snug anchor against the insertion sheath and the artery and retract sheath and deploy and cinch the plug. Other actuations can still happen automatically, such as suture tensioning, controlled travel for cinching and deployment, and releasing of the suture, in keeping with the present invention. Mechanical advantage can be incorporated if desired.

An alternate embodiment utilizes sliding finger hooks, where the finger hooks slide in channels in the handle, where the sliding action automatically actuates a short distance retraction to provide the gap for plug deployment.

For plug materials which are more compressible, an automatic pre-compression action can be provided to pre-compress the plug prior to retraction of the sheaths.

Alternative cinch mechanisms other than the cinch disk include a cinch knot, a friction disk, a crimp, a friction tube, thermal forming, and elastic "spring" actuation, and combinations.

The plug can enhance hemostasis by swelling and physically filling space. Alternatively, the plug can expand from a crumpled, folded or other compressed state to a less-crumpled, folded, or otherwise compressed state to fill space for improved hemostasis. Thrombosis-promoting surfaces, morphology, chemistry, or medication can be incorporated to promote clotting for improved hemostasis. Combinations of hemostasis enhancement means can be utilized.

Indicators can be added to the device to inform the user of certain successful operations, or steps not performed, such as alignment markings, windows, flags, tabs, sounds, colors, snaps and stops felt by the hand, and so forth. These indicators could indicate locking of the hub, seating of the anchor, advancement of the push rod, and so forth.

Various combinations of the cited elements, features, and methods can be utilized, together with other enhancements and features as are known in the art.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A system for installing a vascular closure device, the vascular closure device adapted for sealing an opening in biological tissue and comprising an anchor, a compressible plug, a cinch and a suture, the system comprising:
    a housing attached to the suture;
    a tubular member extending distally from the housing;
    wherein when the anchor is seated against the biological tissue, pulling proximally on the housing causes the tubular member to retract into the housing and expose the plug; and
    a releasable latch between the housing and the tubular member and a compressed biased member, wherein the latch is configured to release at a predetermined force level to allow the compressed biased member to expand to retract the tubular member into the housing.

2. A system for installing a vascular closure device, the vascular closure device adapted for sealing an opening in biological tissue and comprising an anchor, a compressible plug, a cinch and a suture, the system comprising:
    a housing attached to the suture;
    a tubular member extending distally from the housing;
    wherein when the anchor is seated against the biological tissue, pulling proximally on the housing causes the tubular member to retract into the housing and expose the plug;
    a pusher tube disposed in the housing and in the tubular member;
    wherein pulling proximally on the housing causes the pusher tube to move distally with respect to the housing to compress the plug; and
    a releasable latch member and a compressed bias member, wherein the latch is configured to release at a predetermined force level to allow the compressed bias member to expand and force the pusher tube distally to compress the plug.

3. The system of claim 2, further comprising a suture cutting system, the suture cutting system comprising:
- a stop fixed with respect to the housing;
- a shearing block fixed with respect to the tubular member;
- a blade disposed within the block;
- an elongate member attached to the blade and extending proximally therefrom, the elongate member having a proximal end attached to an element disposed about a proximal portion of the pusher tube proximal the stop;
- wherein proximal movement of the pusher tube causes relative movement of the shearing block and blade to cut the suture.

4. The system of claim 3, wherein the suture extends through the blade and the shearing block.

5. A system for installing a vascular closure device, the vascular closure device adapted for sealing an opening in biological tissue and comprising an anchor, a compressible plug, a cinch and a suture, the system comprising:
- a housing attached to the suture;
- a tubular member extending distally from the housing;
- wherein when the anchor is seated against the biological tissue, pulling proximally on the housing causes the tubular member to retract into the housing and expose the plug; and
- a first releasable latch between the housing and the tubular member and a first compressed biased member, wherein the first latch is configured to release at a first predetermined force level to allow the first compressed biased member to expand to retract the tubular member into the housing and a second releasable latch member and a second compressed bias member, wherein the second latch is configured to release at a predetermined force level to allow the second compressed bias member to expand and force the pusher tube distally to compress the plug;
- wherein the second predetermined force level is greater than the first predetermined force level.

6. A system for installing a vascular closure device, the vascular closure device adapted for sealing an opening in biological tissue and comprising an anchor, a compressible plug, a cinch and a suture, the system comprising:
- a housing attached to the suture;
- a tubular member extending distally from the housing;
- wherein when the anchor is seated against the biological tissue, pulling proximally on the housing causes the tubular member to retract into the housing and expose the plug; and
- means for automatically seating the anchor on the tubular member.

7. A system for installing a vascular closure device, the vascular closure device adapted for sealing an opening in biological tissue and comprising an anchor, a compressible plug, a cinch and a suture, the system comprising:
- an insertion sheath; and
- a device sheath;
- whereby the insertion sheath and the device sheath are configured such that the advancement of the device sheath over the insertion sheath and the subsequent retraction of the combination of the insertion sheath and the device sheath seat the plug in the opening;
- wherein the insertion sheath comprises an insertion sheath tube, an insertion sheath hub and a bias member compressed between the insertion sheath tube and the insertion sheath hub, whereby the insertion sheath tube and insertion sheath hub are fixed together at a releasable latch point that is released upon the application of a first force and that, when released, allows the bias member to expand.

8. The system of claim 7, wherein the insertion sheath tube has a beveled distal end.

9. The system of claim 7, wherein the bias member is a spring.

10. The system of claim 7, wherein the bias member operates to retract the insertion sheath tube inside the device sheath when the latch is released.

11. The system of claim 7, further comprising a pusher tube attached to the device sheath by a second releasable latch, the pusher tube and the device sheath together confining a second bias member in a compressed position, the second latch releasable upon application of a second force to allow the second bias member to move the pusher tube distally relative to the device sheath, where the pusher tube has a distal end movable to contact the cinch.

12. The system of claim 11, further comprising means for automatically cutting the suture upon release of the second latch.

13. A method of installing a vascular closure device, the vascular closure device adapted for sealing an opening in biological tissue and comprising an anchor, a compressible plug, a cinch and a suture, the method comprising the steps of:
- providing an insertion sheath;
- inserting the insertion sheath into the opening in the biological tissue;
- providing a device sheath having the vascular closure device preloaded therein with a proximal portion of the suture attached to the device sheath;
- subsequent to the step of inserting the insertion sheath, inserting the device sheath into the insertion sheath; and
- retracting the insertion sheath and device sheath simultaneously, wherein during the retraction, the insertion sheath and the device sheath are fixed to one another;
- wherein the step of retracting the insertion sheath deploys and compresses the plug;
- wherein the step of retracting the insertion sheath cuts the suture.

14. The method of claim 13, further comprising the step of providing a guidewire and wherein the step of inserting the insertion sheath includes the step of inserting the insertion sheath over the guidewire.

15. The method of claim 13, wherein the step of inserting the device sheath into the insertion sheath seats the anchor against a distal end of the insertion sheath.

* * * * *